United States Patent
Wallace et al.

(10) Patent No.: US 7,488,823 B2
(45) Date of Patent: Feb. 10, 2009

(54) CYANOGUANIDINES AND CYANOAMIDINES AS ERBB2 AND EGFR INHIBITORS

(75) Inventors: Eli Wallace, Lyons, CO (US); George Topolov, Superior, CO (US); Qian Zhao, Superior, CO (US); Joseph P. Lyssikatos, Superior, CO (US)

(73) Assignee: Array Biopharma, Inc., Boulder, CO (US)

( * ) Notice: Subject to any disclaimer, the term of this patent is extended or adjusted under 35 U.S.C. 154(b) by 494 days.

(21) Appl. No.: 10/704,120

(22) Filed: Nov. 10, 2003

(65) Prior Publication Data

US 2005/0101617 A1    May 12, 2005

(51) Int. Cl.
C07D 239/84    (2006.01)
C07D 413/04    (2006.01)
A61K 31/517    (2006.01)
A61K 31/4706   (2006.01)
C07D 215/44    (2006.01)

(52) U.S. Cl. .................. 544/284; 544/287; 544/119; 544/313; 514/266.2; 514/266.4; 546/160; 546/162

(58) Field of Classification Search .............. 514/234.5, 514/266.2, 266.3, 266.4, 235.2, 311, 312, 514/313; 544/116, 283, 284, 287, 119; 546/134, 546/135
See application file for complete search history.

(56) References Cited

U.S. PATENT DOCUMENTS

| | | | |
|---|---|---|---|
| 5,112,817 A | 5/1992 | Fukazawa et al. | 514/183 |
| 5,204,348 A | 4/1993 | Fukazawa et al. | 514/253 |
| 5,405,843 A | 4/1995 | Fukazawa et al. | 514/183 |
| 5,821,246 A | 10/1998 | Brown | 514/253 |
| 5,955,464 A | 9/1999 | Barker | 514/253 |
| 6,127,374 A | 10/2000 | Bridges | 514/259 |
| 6,184,225 B1 | 2/2001 | Thomas et al. | 514/259 |
| 6,225,318 B1 * | 5/2001 | Sobolov-Jaynes et al. | 514/266.2 |
| 6,391,874 B1 | 5/2002 | Cockerill et al. | 514/233.5 |
| 7,081,461 B1 | 7/2006 | Mortlock et al. | 514/266.31 |
| 2002/0042409 A1 | 4/2002 | Luzzio et al. | 514/266.4 |
| 2002/0169165 A1 | 11/2002 | Kath et al. | 514/266.4 |
| 2004/0242604 A1 | 12/2004 | Bhattacharya et al. | 514/266.4 |
| 2005/0043334 A1 * | 2/2005 | Wallace et al. | 514/266.2 |
| 2005/0043336 A1 | 2/2005 | Hennequin et al. | 514/266.4 |
| 2005/0049419 A1 * | 3/2005 | Wallace et al. | 548/241 |
| 2005/0054701 A1 * | 3/2005 | Wallace et al. | 514/379 |
| 2005/0130943 A1 * | 6/2005 | Wallace et al. | 514/151 |
| 2005/0153942 A1 * | 7/2005 | Wallace et al. | 514/151 |
| 2005/0250782 A1 * | 11/2005 | Marlow et al. | 514/252.05 |

FOREIGN PATENT DOCUMENTS

WO    WO 96/09294    3/1996

OTHER PUBLICATIONS

Supplementary European Search Report, issued in Corresponding European Patent Application No. 03768789.4-1211, dated on May 21, 2007.

* cited by examiner

Primary Examiner—James O. Wilson
Assistant Examiner—Tamthom N Truong
(74) Attorney, Agent, or Firm—McDermott Will & Emery LLP

(57) ABSTRACT

Cyanoguanidine quinazoline and cyanoamidine quinazolamine derivatives that are useful in the treatment of hyperproliferative diseases are disclosed. Methods of treating hyperproliferative diseases in mammals are also disclosed.

14 Claims, No Drawings

CYANOGUANIDINES AND CYANOAMIDINES AS ERBB2 AND EGFR INHIBITORS

FIELD OF THE INVENTION

This invention relates to a series of cyanoguanidine quinazoline and cyanoamidine quinazoline derivatives that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

BACKGROUND OF THE INVENTION

The type I receptor tyrosine kinase family consists of four closely related receptors: EFGR (ErbB1 or HER1), ErbB2 (HER2), ErbB3 (HER) and ErbB4 (HER4). These are transmembrane glycoprotein receptors which contain an extracellular ligand binding region and, with the expection of erbB3, an intracellular catalytically active tyrosine kinase domain. These receptors transmit extracellular signals through the cytosol to the nucleus. The extracellular signal is transmitted by ligand binding to the homomeric receptor, with the exception of erbB2, of which a high affinity soluble ligand has yet to be identified. After ligand binding the type I receptor tyrosine kinases either homodimerize or heterodimerize with another member of the subfamily of receptors. ErbB2 participates in this process by heteromerization. In fact, it has been shown that erbB2 is the preferred heterodimerization partner (Mendelsohn, J., et al. "The EGF receptor family as targets for cancer therapy." Oncogene. Vol. 19, No. 56 (Dec. 27, 2000): pp. 6550-6565). Dimerization leads to activation by autophosphorylation of the intracellular domain. This autophosphorylation recruits other proteins and leads to a phosphorylation cascade that transmits the signal throughout the cell. The type I receptor tyrosine kinase family signals through the ras/raf/MEK/MAPK pathway as well as the P13K/Akt pathway. These signaling pathways lead to both cell proliferation and cell survival through inhibition of apoptosis.

Several investigations have demonstrated the role of EGFR and ErbB2 in cancer. Squamous carcinomas of the head and neck, and lung express high levels of EGFR. Also, constitutively active EGFR has been found in gliomas, breast cancer and lung cancer (Salomon, David S., et al. "Epidermal growth factor-related peptides and their receptors in human malignancies." Crit. Rev. Oncology/Hematology. Vol. 19, Issue 3 (July 1995): pp. 183-232). ErbB2 overexpression occurs in ~30% of all breast cancer. It has been also implicated in other human cancers including colon, ovary, bladder, stomach, esophagus, lung, uterus and prostate. ErbB2 overexpression has also been correlated with poor prognosis in human cancer, including metastasis, and early relapse (Slamon, DJ, et al. "Studies of the Her-2/neu proto-oncogene in human breast and ovarian cancer." Science. Vol. 244, No. 4905 (May 1989): pp. 707-712; Slamon, DJ, et al. "Human breast cancer: correlation of relapse and survival of the HER-2/neu oncogene." Science, Vol. 235, No. 4785 January 1987): pp. 177-182; Klapper, LN, et al. "Biochemical and clinical implications of the ErbB/HER signaling network of growth factor receptors," Adv. Cancer Res. 77(2000): pp. 25-79).

The type I tyrosine kinase receptor family has been an active area of anti-cancer research. Several inhibitors of the EGFR and the ErbB2 signaling pathway have demonstrated clinical efficacy in cancer treatment. Herceptin, a humanized version of anti-ErbB2 monoclonal antibody, was approved for use in breast cancer in the United States in 1998. Iressa and Tarceva are small molecule inhibitors of EGFR that are expected to be launched in 2002. In addition, several other antibodies and small molecules that target the interruption of the type I tyrosine kinase receptor signaling pathways are in clinical and preclinical development (Ciardiello, F., et al, "Antitumor effects of ZD6474, a Small Molecule Vascular Endothelial Growth Factor Receptor Tyrosine Kinase Inhibitor, with Additional Activity against Epidermal Growth Factor Receptor Tyrosing Kinase." Clin. Cancer Res. Vol. 9 (April 2003): pp. 1546-1556).

Several issued patents and applications have appeared describing quinazoline based type I receptor tyrosine kinase inhibitors, including WO 00/44728, WO 01/98277, WO 98/02438, GB 2 345 486 A, WO 96/33980, and references contained therein, which are incorporated herein by reference.

SUMMARY OF THE INVENTION

This invention provides for cyanoguanidine and cyanoamidine substituted 4-anilino quinazolines of formula I, and pharmaceutically acceptable salts and prodrugs thereof, that are useful in the treatment of hyperproliferative diseases. Specifically, the present invention relates to compounds of formula I that act as EGFR and/or ErbB2 inhibitors. Also provided are formulations containing compounds of formula I and methods of using the compounds to treat a patient in need thereof. In addition, there are described processes for preparing the inhibitory compounds of formula I.

Accordingly, the present invention refers to compounds of the formula (I):

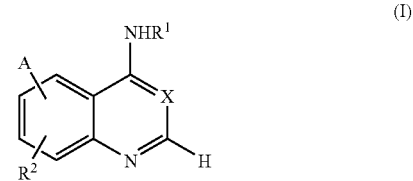

wherein at least one of the positions 6 or 7 of the quinazoline ring must be substituted by a group A, and the remaining positions on the quinazoline ring may be optionally substituted by up to three $R^2$ groups; wherein X is N, CH or a C—CN group;

$R^1$ is independently an aryl or heteroaryl group, substituted by at least one one $R^6$ group, and optionally substituted by up to three $R^5$ groups, where $R^5$ is cyano, chlorine, fluorine, bromine, lower alkyl, trifluoromethyl, difluoromethyl, nitro or $OR^9$;

$R^6$ is hydrogen, cyano, chlorine, fluorine, bromine, trifluoromethyl, difluoromethyl, trifluoromethoxy, nitro, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, where each $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl portion is optionally substituted with up to five groups independently selected from oxo, halogen, cyano, nitro, trifluoromethyl, difluoromethoxy, trifluoromethoxy, azido, —$NR^7SO_2R^8$, —$SO_2NR^9R^7$, —$C(O)R^9$, —$C(O)OR^9$, —$OC(O)R^9$, —$NR^7C(O)OR^8$, —$NR^7C(O)R^9$, —$C(O)NR^7R^9$, —$NR^7R^9$, —NR$^{10}$C(O)NR$^7$R$^9$, —OR$^9$, —S(O)R$^3$, —SO$_2$R$^3$, aryl, arylalkyl, heteroaryl, heteroarylalkyl, heterocyclyl, and heterocyclylalkyl, and where R$^7$ and R$^{10}$ independently represent hydrogen or C$_{1-6}$ alkyl, or R$^7$ and R$^{10}$ together with the atom to which they are attached form a 4 to 10 membered carbocyclic, heteroaryl or heterocyclic ring, each of which is optionally substituted with up to three groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

R$^8$ represents trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, where each alkyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, aryl, heteroaryl, arylalkyl, heteroarylalkyl, heterocyclyl or heterocyclylalkyl;

R$^9$ represents represents hydrogen, trifluoromethyl, C$_1$-C$_{10}$ alkyl, (CH$_2$)$_n$C$_3$-C$_{10}$ cycloalkyl, aryl, arylalkyl, heteroaryl, heteroarylalkyl, heterocyclyl or heterocyclylalkyl, where each alkyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, aryl, heteroaryl, arylalkyl, heteroarylalkyl, heterocyclyl and heterocyclylalkyl, where n=0 or 4, or R$^7$ and R$^9$ together with the atom to which they are attached form a 4 to 10 membered carbocyclic, heteroaryl or heterocyclic ring, each of which is optionally substituted with up to three groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

R$^{13}$ represents trifluoromethyl, difluoromethyl, C$_1$-C$_{10}$ alkyl, C$_3$-C$_{10}$ alkenyl, C$_3$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, where each of the above alkyl, alkenyl, alkynyl, cycloalkyl, aryl, heteroaryl and heterocyclyl portion of R$^{13}$ is optionally substituted with one to five groups independently selected from oxo, halogen, cyano, nitro, trifluoromethyl, difluoromethoxy, trifluoromethoxy, azido, —NR$^7$SO$_2$R$^8$, —SO$_2$NR$^9$R$^7$, —C(O)R$^9$, —C(O)OR$^9$, —OC(O)R$^9$, —NR$^7$C(O)OR$^8$, —NR$^7$C(O)R$^9$, —C(O)NR$^7$R$^9$, —NR$^7$R$^9$, —NR$^{10}$C(O)NR$^7$R$^9$, —NR$^{10}$C(NCN)NR$^7$R$^9$, —OR$^9$, aryl, arylalkyl, heteroaryl, heteroarylalkyl, heterocyclyl and heterocyclylalkyl; where R$^7$, R$^8$, R$^9$ and R$^{10}$ are the same as R$^7$, R$^8$, R$^9$ and R$^{10}$ defined above;

R$^2$ represents hydrogen, halogen, cyano, nitro, trifluoromethyl, difluoromethyl, trifluoromethoxy, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —NR$^7$SO$_2$R$^8$, —SO$_2$NR$^9$R$^7$, —C(O)R$^9$, —C(O)OR$^9$, —OC(O)R$^9$, —NR$^7$C(O)OR$^8$, —NR$^7$C(OCR$^9$, —C(O)NR$^7$R$^9$, —NR$^7$R$^9$, —NR$^{10}$C(O)NR$^7$R$^9$, —NR$^{10}$C(NCN)NR$^7$R$^9$, —OR$^9$, —S(O)R$^3$, —SO$_2$R$^{13}$, aryl, arylalkyl, heteroaryl, heteroarylalkyl, heterocyclyl and heterocyclylalkyl, and where R$^7$, R$^8$, R$^9$, R$^{10}$ and R$^{13}$ are the same as R$^7$, R$^8$, R$^9$, R$^{10}$ and R$^{13}$ as defined above;

A is represented by the following formula (II):

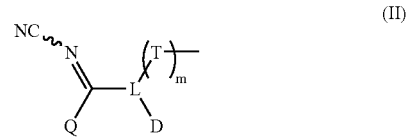

(II)

wherein

T represents C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl; where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —NR$^7$SO$_2$R$^8$, —SO$_2$NR$^9$R$^7$, —C(O)R$^9$, —C(O)OR$^9$, —OC(O)R$^9$, —NR$^7$C(O)OR$^8$, —NR$^7$C(O)R$^9$, —C(O)NR$^7$R$^9$, —NR$^7$R$^9$, —NR$^{10}$C(O)NR$^7$R$^9$, —NR$^{10}$C(NCN)NR$^7$R$^9$, —OR$^9$, —S(O)R$^{13}$, —SO$_2$R$^{13}$, aryl, arylalkyl, heteroaryl, heteroarylalkyl, heterocyclyl and heterocyclylalkyl, where R$^7$, R$^8$, R$^9$, R$^{10}$ and R$^{13}$ are the same as R$^7$, R$^8$, R$^9$, R$^{10}$ and R$^{13}$ as defined above; T may optionally contain one or more heteroatoms, which heteroatoms may be further substituted or oxidized; and m is an integer from 0 to 1;

L is a nitrogen atom or a CR$^4$ group where R$^4$ represents hydrogen, trifluoromethyl, difluoromethyl, trifluoromethoxy, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —NR$^7$SO$_2$R$^8$, —SO$_2$NR$^9$R$^7$, —C(O)R$^9$, —C(O)OR$^9$, —OC(O)R$^9$, —NR$^7$C(O)OR$^8$, —NR$^7$C(OCR$^9$, —C(O)NR$^7$R$^9$, —NR$^7$R$^9$, —NR$^{10}$C(O)NR$^7$R$^9$, —NR$^{10}$C(NCN)NR$^7$R$^9$, —OR$^9$, —S(O)R$^{13}$, —SO$_2$R$^{13}$, aryl, arylalkyl, heteroaryl, heteroarylalkyl, heterocyclyl and heterocyclylalkyl; where R$^7$, R$^8$, R$^9$, R$^{10}$ and R$^{13}$ are the same as R$^7$, R$^8$, R$^9$, R$^{10}$ and R$^{13}$ defined above;

Q is selected from CR$^3$R$^{11}$R$^{12}$ or NR$^{11}$R$^{12}$, where R$^3$ is the same as R$^2$ defined above and R$^{11}$ and R$^{12}$ independently represent hydrogen, trifluoromethyl, difluoromethyl, trifluoromethoxy, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, —NR$^7$SO$_2$R$^8$, —SO$_2$NR$^9$R$^7$, —C(O)R$^9$, —C(O)OR$^9$, —OC(O)R$^9$, —NR$^7$C(O)OR$^8$, —NR$^7$C(O)R$^9$, —C(O)NR$^7$R$^9$, —NR$^7$R$^9$, —NR$^{10}$C(O)NR$^7$R$^9$, —OR$^9$, —S(O)R$^{13}$ or —SO$_2$R$^{13}$, where each C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl and heterocyclylalkyl portion may be optionally substituted with up to five groups independently selected from oxo, halogen, cyano, nitro, trifluoromethyl, difluoromethoxy, trifluoromethoxy, azido, —NR$^7$SO$_2$R$^8$, —SO$_2$NR$^9$R$^7$, —C(O)R$^9$, —C(O)OR$^9$, —OC(O)R$^9$, —NR$^7$C(O)OR$^8$, —NR$^7$C(O)R$^9$, —C(O)NR$^7$R$^9$, —NR$^7$R$^9$, —NR$^{10}$C(O)NR$^7$R$^9$, —NR$^{10}$C(NCN)NR$^7$R$^9$, —OR$^9$, —S(O)R$^{13}$, —SO$_2$R$^{13}$, aryl, arylalkyl, heteroaryl, heteroarylalkyl, heterocyclyl and heterocyclylalkyl; where R$^7$, R$^8$, R$^9$, R$^{10}$ and R$^{13}$ are the same as R$^7$, R$^8$, R$^9$, R$^{10}$ and R$^{13}$ defined above, provided that (i) when Q is CR$^3$R$^{11}$R$^{12}$ not more than one group among R$^3$, R$^{11}$ or R$^{12}$ may be simultaneously connected to C through a heteroatom, (ii) when Q is $CR^3R^{11}R^{12}$, $R^3$ may not be cyano or halogen, (iii) when Q is $NR^{11}R^{12}$, not more than one group between $R^{11}$ and $R^{12}$ may be connected to N through a heteroatom, and (iv) when L is $CR^4$, Q is $NR^{11}R^{12}$; and D represents hydrogen, trifluoromethyl, difluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, $-SO_2NR^9R^7$, $-C(O)R^9$, $-C(O)OR^9$, $-OC(O)R^9$ or $-C(O)NR^7R^9$, where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, $-NR^7SO_2R^8$, $-SO_2NR^9R^7$, $-C(O)R^9$, $-C(O)OR^9$, $-OC(O)R^9$, $-NR^7C(O)OR^8$, $-NR^7C(O)R^9$, $-C(O)NR^7R^9$, $-NR^7R^9$, $-NR^{10}C(O)NR^7R^9$, $-NR^{10}C(NCN)NR^7R^9$, $-OR^9$, $-S(O)R^{13}$, $-SO_2R^{13}$, aryl, arylalkyl, heteroaryl, heteroarylalkyl, heterocyclyl and heterocyclylalkyl, and where $R^7$, $R^8$, $R^9$, $R^{10}$ and $R^{13}$ are the same as $R^7$, $R^8$, $R^9$, $R^{10}$ and $R^{13}$ defined above, provided that when L is N, (i) D is hydrogen or is selected so that L binds to a carbon atom or to a $S(O)_i$ group, where i is an integer from 1 to 2, and (ii) if m=1, T is selected so that L binds to a carbon atom or to a $S(O)_j$ group, where j is an integer from 1 to 2; or Q and D taken together form a 5-11 member ring containing 0-3 heteroatoms in addition to the nitrogen atoms which are part of the cyanoguanidine or cyanoamidine group, with no direct bonding between any two heteroatoms, except for a bond between N to $S(O)_k$, where k is an integer from 1 to 2, the carbon atoms of the said ring optionally substituted with up to two groups selected from oxo, halogen, cyano, nitro, trifluoromethyl, difluoromethoxy, trifluoromethoxy, azido, aryl, arylalkyl, heteroaryl, heteroarylalkyl, heterocyclyl, heterocyclylalkyl, alkyl, alkenyl, alkynyl, cycloalkyl, $-NR^7SO_2R^8$, $-SO_2NR^9R^7$, $-C(O)R^9$, $-C(O)OR^9$, $-OC(O)R^9$, $-NR^7C(O)OR^8$, $-NR^7C(O)R^9$, $-C(O)NR^7R^9$, $-NR^7R^9$, $-NR^{10}C(O)NR^7R^9$, $-NR^{10}C(NCN)NR^7R^9$, $-OR^9$, $-S(O)R^{13}$, and $-SO_2R^{13}$, where $R^7$, $R^8$, $R^9$, $R^{10}$ and $R^{13}$ are the same as $R^7$, $R^8$, $R^9$, $R^{10}$ and $R^{13}$ above, and each nitrogen atom of the said ring may be optionally and independently substituted with an $R^4$ group, where $R^4$ is the same as $R^4$ defined above.

Examples of preferred embodiments of $R^2$ include, but are not limited to:

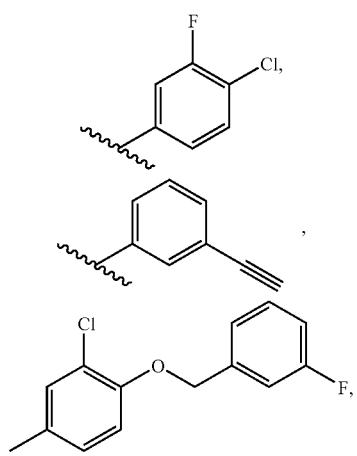

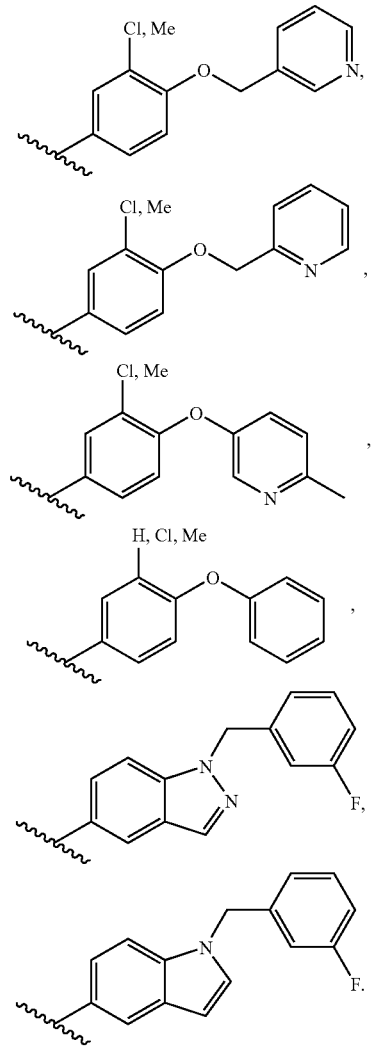

In another aspect of the invention there is provided a method of treating hyperproliferative disease comprising administering to a mammal a therapeutically effective amount of a compound of the invention.

DETAILED DESCRIPTION OF THE INVENTION

The novel compounds encompassed by the instant invention are those described by the general formula I set forth above, including enantiomers, diastereosisomers, tautomers, pharmaceutically acceptable salts, and prodrugs thereof.

Except as expressly defined otherwise, the following definition of terms is employed throughout this specification.

By "$C_1$-$C_{10}$ alkyl", "alkyl" and "lower alkyl" in the present invention is meant straight or branched chain alkyl groups having 1-10 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, heptyl, octyl, and the like. Preferred alkyl radicals are $C_{1-6}$ alkyls. More preferred alkyl radicals are $C_{1-3}$ alkyls.

By "$C_2$-$C_{10}$ alkenyl", "lower alkenyl" and "alkenyl" means straight and branched hydrocarbon radicals having from 2 to 10 carbon atoms and at least one double bond and includes ethenyl, propenyl, 1-but-3-enyl, 1-pent-3-enyl, 1-hex-5-enyl and the like. The preferred alkenyls are lower alkenyl having 3-5 carbon atoms.

By "$C_2$-$C_{10}$ alkynyl", "lower alkynyl" and "alkynyl" means straight and branched hydrocarbon radicals having from 2 to 10 carbon atoms and at least one triple bond and includes ethynyl, propynyl, butynyl, pentyn-2-yl and the like. The preferred alkynyls are alkynyl having 3-5 carbon atoms.

By the term "halogen" in the present invention is meant fluorine, bromine, chlorine, and iodine.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

By "heteroaryl" is meant one or more aromatic ring systems of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

As used herein, the terms "carbocycle", "carbocyclyl", "cycloalkyl" or "$C_3$-$C_{10}$ cycloalkyl" refer to saturated carbocyclic radicals having three to ten carbon atoms. The cycloalkyl can be monocyclic, or a polycyclic fused system, and can be fused to an aromatic ring. Examples of such radicals include cyclopropyl, cyclobutyl, cyclopentyl and cyclohexyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heterocycle" or "heterocyclyl" is meant one or more carbocyclic ring systems of 5-, 6-, or 7-membered rings which includes fused ring systems of 4-10 atoms containing at least one and up to four heteroatoms selected from nitrogen, oxygen, or sulfur, and with the proviso that the ring of the group does not contain two adjacent O or S atoms. A fused system can be a heterocycle fused to an aromatic group. Preferred heterocycles include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]-hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "arylalkyl" means an alkyl moiety (as defined above) substituted with one or more aryl moiety (also as defined above). The preferred aralkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). The preferred heteroarylalkyl radicals are 5- or 6-membered heteroaryl-$C_{1-3}$-alkyl. Examples include oxazolemethyl, pyridylethyl and the like.

The term "Me" means methyl, "Et" means ethyl, "Bu" means butyl and "Ac" means acetyl.

The phrase "pharmaceutically acceptable salt(s)", as used herein, unless otherwise indicated, includes salts of acidic and basic groups which may be present in the compounds of formula 1 or of the compounds made in accordance with the examples herein. The compounds of formula 1 that are basic in nature are capable of forming a wide variety of salts with various inorganic and organic acids. The acids that may be used to prepare pharmaceutically acceptable acid addition salts of such basic compounds of formula 1 as well as the compounds prepared in the examples are those that form non-toxic acid addition salts, i.e., salts containing pharmaceutically acceptable anions, such as the acetate, benzenesulfonate, benzoate, bicarbonate, bisulfate, bitartrate, borate, bromide, calcium, edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palimitate, pantothenate, phosphate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

The phrase "pharmaceutically acceptable salt(s)", as used herein, unless otherwise indicated, includes salts of acidic and basic groups which may be present in the compounds of formula 1. The compounds of formula I that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmaceutically acceptable anions, such as the acetate, benzenesulfonate, benzoate, bicarbonate, bisulfate, bitartrate, borate, bromide, calcium, edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palimitate, pantothenate, phosphate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

Those compounds of the present invention that are acidic in nature are capable of forming basic salts with various pharmaceutically acceptable cations. Examples of such salts include the alkali metal or alkaline earth metal salts and, particularly, the calcium, magnesium, sodium and potassium salts of the compounds of the present invention.

Certain compounds of formula I may have asymmetric centers and therefore exist in different enantiomeric forms. All optical isomers and stereoisomers of the compounds of formula I, and mixtures thereof, are considered to be within the scope of the invention. With respect to the compounds of formula I, the invention includes the use of a racemate, one or more enantiomeric forms, one or more diastereomeric forms, or mixtures thereof. The compounds of formula I may also exist as tautomers. This invention relates to the use of all such tautomers and mixtures thereof.

The subject invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Futher, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compound of formula I of this invention and prodrugs thereof can generally be prepared by carrying out procedures disclosed in the Schemes and/or in the Examples and Preparations below, by substituting a readily available isotopically labeled reagent for a non-isotopically labeled reagent.

This invention also encompasses pharmaceutical compositions containing and methods of treating proliferative disorders, or abnormal cell growth, by administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

The compounds of the invention are administered either singly or in combination to a mammal to treat hyperproliferative disease, such as various types of cancer, e.g., cancer of the colon, ovary, bladder, stomach, lung, uterus, and prostate. The compound may be administered via any acceptable route, e.g., intra venous, oral, intra muscular, via suppository, etc. The compounds can be formulated as oral dosage forms, e.g., tablets, capsules, liquid suspension, etc, as suppositories, or may be prepared as a liquid for injection, for example. The skilled practitioner can select the appropriate route and dosage amount for treatment of the specific hyperproliferative disease to be treated.

The examples below are intended to illustrate embodiments of the invention, and are not intended to limit the scope of the specification or claims in any way.

EXAMPLE 1

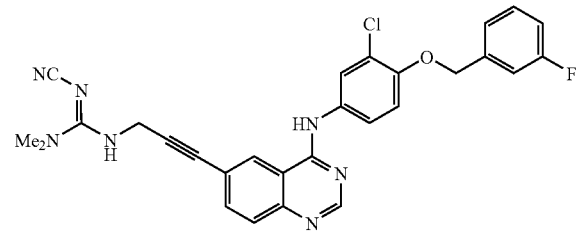

N-(3-{4-[3-Chloro-4-(3-fluoro-benzyloxy)-phenylamino]-quinazolin-6-yl}-prop-2-ynyl)-N'-cyano-N",N"-dimethylguanidine Step A: 6-iodo-4-quinazolinone.

A solution of 2-amino-5-iodobenzoic acid (14.2 g, 50 mmol) and formamidine acetate (6.75 g, 65 mmol) in ethanol (200 mL) was refluxed for 20 hours. After cooling to 0° C. the solid product was collected by filtration. Further drying in a vacuum provided 6-Iodo-4-quinazolinone (11 g, 81%) as a gray solid.

Step B: 4-chloro-6-iodoquinazoline.

To a stirred solution of anhydrous dimethyl foramide (DMF) (3.20 ml) in 1,2-dichloroethane (DCE) (10 ml), cooled in an ice-water bath, is added dropwise under nitrogen a solution of oxalyl chloride (5.2 ml, 60 mmol) in DCE (25 ml). A white precipitate forms during the addition. After the end of addition the cold bath is removed and the reaction mixture is stirred at room temperature for 5 minutes. 6-Iodoquinazolin-4-ol (5.0 g, 18 mmol) is added in portions via scoopula under nitrogen flow and the mixture is heated immediately to reflux. Heating is continued for 4.5 hours, followed by cooling to room temperature. The reaction mixture is poured into excess ice-water mixture (approximately 300 ml) and extracted with DCM (approximately 500 ml). The aqueous layer is further extracted with DCM (2×50 ml). The combined organic extracts are dried ($Na_2SO_4$) and concentrated under reduced pressure to yield 5.2 g (99%) of desired product as a tan solid.

Step C: 2-chloro-1-(3-fluoro-benzyloxy)-4-nitro-benzene.

Sodium hydride (60% dispersion in oil, 1.4 g, 33.5 mmol) is suspended in dry DMF (10 ml) under a nitrogen atmosphere and the resulting mixture is cooled in ice:water. To above suspension is added dropwise over 15 minutes (3-Fluorophenyl)-methanol (2.90 ml, 27 mmol). Next, to the cold reaction mixture is added dropwise over 20 minutes a solution of 2-chloro-1-fluoro-4-nitro-benzene (4.2 g, 24 mmol) in dry DMF (20 ml). Upon the end of addition the cold bath is removed and the reaction mixture is stirred for another 4 hours. The reaction mixture is poured into 300 ml of ice:water. The resultant solid is isolated by suction filtration, washed with water (500 ml), and air dried to yield 5.5 g (20 mmol, 83%) of the clean desired material as an yellow powder.

Step D: 3-chloro-4-(3-fluoro-benzyloxy)-phenylamine.

2-Chloro-1-(3-fluoro-benzyloxy)-4-nitro-benzene (4.08 g, 14.5 mmol) is suspended in MeOH (50 ml) and treated wet 5% Pt/C (Degussa type, Aldrich, 1.5 g). The flask is flushed with hydrogen gas from a balloon and the reaction mixture is stirred under hydrogen atmosphere until reaction is judged complete by this-layer chromatography (approximately 2 hours). The reaction mixture is filtered through a Celite plug and the solvent is removed under reduced pressure. The crude product is redissolved in DCM, dried ($MgSO_4$) and concentrated to yield 3.1 g (12 mmol, 83%) of the desired product.

Step E: [3-chloro-4-(3-fluoro-benzyloxy)-phenyl]-(6-iodo-quinazolin-4-yl)-amine hydrochloride salt.

3-Chloro-4-(3-fluoro-benzyloxy)-phenylamine (3.1 g, 12 mmol) and 4-chloro-6-iodo-quinazoline (3.28 g, 11.3 mmol) are dissolved in a 1:1 mixture of DCE:t-BuOH (56 ml). The reaction mixture is refluxed for 19 hours. The product is isolated by suction filtration through sintered glass, washed with excess DCM, and air dried to afford 3.8 g (7.0 mmol, 58%) of the clean desired material.

Step F: (3-{4-[3-chloro-4-(3-fluoro-benzyloxy)-phenylamino]-quinazolin-6-yl}-prop-2-ynyl)-carbamic acid tert-butyl ester.

A mixture of prop-2-ynyl-carbamic acid tert-butyl ester (978 mg, 6.31 mmol) and 3-chloro-4-(3-fluoro-benzyloxy)-phenylamine hydrochloride (3.11 g, 5.74 mmol), dichlorobis (tri-phenylphosphine) palladium (II) (210 mg, 0.299 mmol), copper iodide (57 mg, 0.3 mmol), and diisopropylamine (1.77 mL, 7.28 mmol) in anhydrous THF (40 mL) was stirred at room temperature for 5 hours. After concentration, the residue was dissolved in $CH_2Cl_2$ (50 mL), washed with aqueous $NH_4Cl$ and brine, dried over sodium sulfate, and concentrated to give the crude product (3.07 g, 100%) as a light yellow solid which was then used without further purification.

Step G: [6-(3-amino-prop-1-ynyl)-quinazolin-4-yl]-[3-chloro-4-(3-fluoro-benzyloxy)-phenyl]-amine.

To a suspension of (3-{4-[3-chloro-4-(3-fluoro-benzyloxy)-phenylamino]-quinazolin-6-yl}-prop-2-ynyl)-carbamic acid tert-butyl ester (2.01 g, 3.78 mmol) in $CH_2Cl_2$ (3 mL) was added trifluoroacetic acid (TFA) (3 mL) dropwise. The reaction was stirred at room temperature for 30 minutes. The reaction mixture was then diluted with $CH_2Cl_2$ (30 mL) and aqueous saturated sodium bicarbonate. Phases were separated and the aqueous layer was extracted with $CH_2Cl_2$ (30 mL). Organic layers were combined, dried over sodium sulfate and concentrated to give the crude product (1.648 g, 101%) as a yellow oil.

Step H: 1-(3-{4-[3-chloro-4-(3-fluoro-benzyloxy)-phenylamino]-quinazolin-6-yl}-prop-2-ynyl)-2-phenyl-N-cyano-isourea.

A mixture of [6-(3-amino-prop-1-ynyl)-quinazolin-4-yl]-[3-chloro-4-(3-fluoro-benzyloxy)-phenyl]-amine (520 mg, 1.2 mmol), diphenyl cyano-carbonimidate (315 mg, 1.32 mmol), and triethylamine (0.17 mL, 1.2 mmol) in isopropanol (10 mL) was stirred at room temperature for 15 hours. After concentration, the crude white residue (840 mg) was then used without further purification.

Step I: N-(3-{4-[3-Chloro-4-(3-fluoro-benzyloxy)-phenylamino]-quinazolin-6-yl}-prop-2-ynyl)-N'-cyano-N",N"-dimethylguanidine.

A mixture of crude 1-(3-{4-[3-chloro-4-(3-fluoro-benzyloxy)-phenylamino]-quinazolin-6-yl}-prop-2-ynyl)-2-phenyl-N-cyano-isourea (80 mg, 0.14 mmol), dimethylamine (0.25 mL, 2M in THF) in isopropanol (3 mL) was heated to 85° C. in a sealed tube. The reaction was cooled to room temperature after 3 hours. Solvent was removed via rotovap. The residue was then purified by FCC to give the final product (35 mg, 47%) as a light yellow solid. MS ESI (+) m/z 528 (M+1) detected; $^1H$ NMR (400 MHz, deuterated DMSO) 9.9 (s, 1H), 8.7 (s, 1H), 8.6 (s, 1H), 8.05 (s, 1H), 7.8 (m, 1H), 7.75 (m, 2H), 7.58 (br, 1H), 7.5 (m, 1H), 7.22-7.4 (m, 3H), 7.2 (m, 1H), 5.25 (s, 2H), 4.4 (m, 2H), 3.02 (s, 6H).

EXAMPLE 2

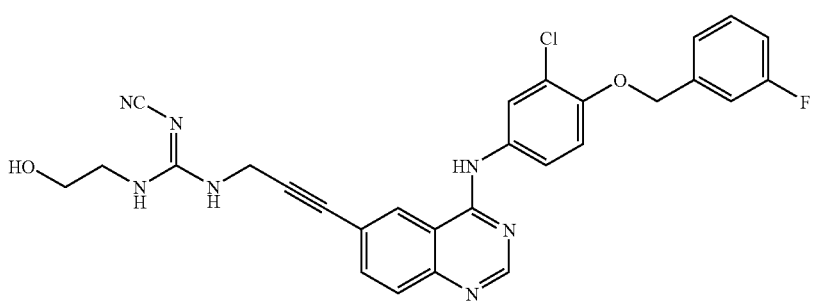

N-(3-{4-[3-Chloro-4-(3-fluoro-benzyloxy)-phenylamino]-quinazolin-6-yl}-prop-2-ynyl)-N'-cyano-N''-3-(2-hydroxy-ethyl)guanidine.

A mixture of crude 1-(3-{4-[3-chloro-4-(3-fluoro-benzyloxy)-phenylamino]-quinazolin-6-yl}-prop-2-ynyl)-2-phenyl-N-cyano-isourea (70 mg, 0.12 mmol) (from Step H, Example 1), 2-hydroxyethylamine hydrochloride (39 mg, 0.4 mmol) and triethylamine (0.07 mL, 0.5 mmol) in isopropanol (2 mL) was heated to 85° C. in a sealed tube. The reaction was cooled to room temperature after 3 hours. Solvent was removed via rotovap. The residue was then purified by FCC to give the final product (25 mg, 38%) as a light yellow solid. MS ESI (+) m/z 544 (M+1) detected; $^1$H NMR (400 MHz, deuterated DMSO) 9.95 (s, 1H), 8.7 (s, 1H), 8.6 (s, 1H), 8.05 (s,1H), 8.0 (s, 1H), 7.8 (m, 1H), 7.78 (m, 2H), 7.6 (br, 1H), 7.5 (m, 1H), 7.22-7.4 (m, 2H), 7.2 (m, 1H), 7.1 (m, 1H), 5.25 (s, 2H), 4.25 (m, 2H), 3.5 (m, 2H), 3.25 (m, 2H).

EXAMPLE 3

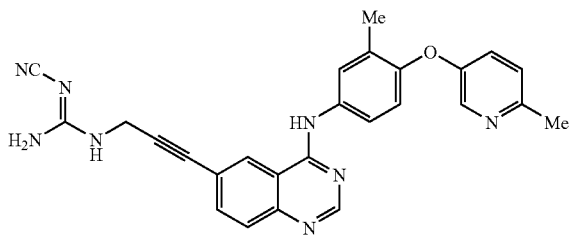

N-cyano-N'-(3-{4-[3-Methyl-4-(6-methyl-pyridin-3-yloxy)-phenylamino]-quinazolin-6-yl}-prop-2-ynyl) guanidine

Step A: 2-methyl-5-(2-methyl-4-nitro-phenoxy)-pyridine.

To a 500 mL flask equipped with addition funnel at 0° C. was added NaH (8.26 g, 95%, 327 mmol), followed by slow addition of DMF (100 mL). The mixture was stirred for 10 minutes. The addition funnel was then charged with 6-methyl-pyridin-3-ol (30.2 g, 277 mmol) and DMF (100 mL), and the solution in addition funnel was added to the flask dropwise over 45 minutes. The reaction mixture was stirred at 0oC. for another 30 minutes once the addition was finished. To the addition funnel was then added 4-fluoro-3-methyl-nitrobenzene (39.1 g, 252 mmol) and DMF (100 mL) and the resulting solution was added to the flask dropwise over 45 minutes. The cold bath was removed at the end of the addition and the reaction mixture was allowed to stir at room temperature for 15 hours. The red dark solution was cooled to 0° C. and water (100 mL) was added cautiously to the reaction mixture. The resulting solution was stirred for 30 minutes and solid product was purified by filtration and washed with cold water (500 mL). The wet solid was dried in vacuo to give product (49.8 g, 81%).

Step B: 3-methyl-4-(6-methyl-pyridin-3-yloxy)-phenylamine

A mixture of 2-methyl-5-(2-methyl-4-nitro-phenoxy)-pyridine (11.5 g, 47.1 mmol) and palladium on carbon (300 mg, 10 wt. %, wet) in MeOH (200 mL) was flashed with hydrogen. A hydrogen balloon was then applied to the reaction mixture. The reaction was stirred for 2 hours and the solution was filtered through a pad of celite, and the pad was washed with MeOH (300 mL). Concentration of the solution gave crude product (8.8 g, 87%) as light yellow solid.

Step C: (6-iodo-quinazolin-4-yl)-[3-methyl-4-(6-methyl-pyridin-3-yloxy)-phenyl]-amine hydrochloride

A mixture of 3-methyl-4-(6-methyl-pyridin-3-yloxy)-phenylamine (4.96 g, 23.18 mmol), 4-Chloro-6-iodo-quinazoline 604 g, 22.06 mmol) in tBuOH (60 mL) and DCE (60 mL) was refluxed for 6 hours. The reaction was cooled to 0° C. and the solid product (8.44 g, 76%) was isolated by filtration and washed with cold CH$_2$Cl$_2$ (50 mL).

Step D: (3-{4-[3-Methyl-4-(6-methyl-pyridin-3-yloxy)-phenylamino]-quinazolin-6-yl}-prop-2-ynyl)-carbamic acid tert-butyl ester.

A mixture of prop-2-ynyl-carbamic acid tert-butyl ester (2.65 g, 17.08 mmol) and (6-Iodo-quinazolin-4-yl)-[3-methyl-4-(6-methyl-pyridin-3-yloxy)-phenyl]-amine hydrochloride (8.2 g, 16.27 mmol), dichlorobis(triphenylphosphine) palladium (II) (570 mg, 0.81 mmol), copper iodide (154 mg, 0.81 mmol), and diisopropylamine (4.78 mL, 34.16 mmol) in anhydrous THF (80 mL) was stirred at room temperature for 5 hours. After concentration, the residue was dissolved in CH$_2$Cl$_2$ (100 mL), washed with aqueous NH$_4$Cl and brine, dried over sodium sulfate, and concentrated to give the crude product (7.89 g, 98%) as a light yellow solid which was then used without further purification.

Step E: [6-(3-Amino-prop-1-ynyl)-quinazolin-4-yl]-[3-methyl-4-(6-methyl-pyridin-3-yloxy)-phenyl]-amine.

To a suspension of (3-{4-[3-methyl-4-(6-methyl-pyridin-3-yloxy)-phenylamino]-quinazolin-6-yl}-prop-2-ynyl)-carbamic acid tert-butyl ester (1.22 g, 2.46 mmol) in CH$_2$Cl$_2$ (3 mL) was added TFA (3 mL) dropwise. The reaction was stirred at room temperature for 30 minutes. The reaction mixture was then diluted with CH$_2$Cl$_2$ (30 mL) and aqueous saturated sodium bicarbonate. Phases were separated and the aqueous layer was extracted with CH$_2$Cl$_2$ (30 mL). Organic layers were combined, dried over sodium sulfate and concentrated to give the crude product (0.85 g, 88%) as a yellow oil.

Step F: N-cyano-N'-(3-{4-[3-Methyl-4-(6-methyl-pyridin-3-yloxy)-phenylamino]-quinazolin-6-yl}-prop-2-ynyl)guanidine.

A mixture of 2-phenyl-N-cyano-isourea (50 mg, 0.31 mmol) and [6-(3-amino-prop-1-ynyl)-quinazolin-4-yl]-[3-methyl-4-(6-methyl-pyridin-3-yloxy)-phenyl]-amine (30 mg, 0.076 mmol) in isopropanol (3 mL) was heated at 85° C. in a sealed tube. The reaction was cooled to room temperature after 5 hours. Solvent was removed via rotovap. The residue was then purified by FCC to give the final product (18 mg, 51%) as a light yellow solid. MS ESI (+) m/z 463 (M+1) detected; $^1$H NMR (400 MHz, deuterated DMSO) □ 9.9 (s, 1H), 8.7 (s, 1H), 8.6 (s, 1H), 8.2 (s, 1H), 7.8 (m, 2H), 7.75 (m, 2H), 7.2 (m, 3H), 7.0 (m, 3H), 4.22 (m, 2H), 2.42 (s, 3H), 2.2 (s, 3H).

EXAMPLE 4

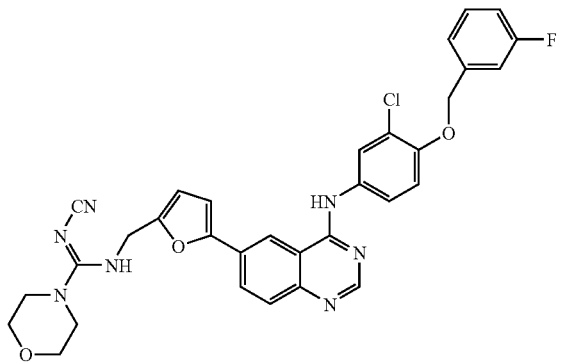

N-(5-{4-[3-Chloro-4-(3-fluoro-benzyloxy)-phenylamino]-quinazolin-6-yl}-furan-2-ylmethyl)-N'-cyano-morpholine-4-carboxamidine Step A: furan-2-ylmethyl-carbamic acid tert-butyl ester.

Furan-2-ylmethylamine (8.0 ml, 91 mmol) and $Boc_2O$ (19.8 g, 91 mmol) are dissolved in DCM (40 ml) and stirred at room temperature for 1.5 hours. The reaction mixture is filtered and concentrated under reduced pressure to afford 17.6 g (85 mmol, 93%) of the desired product as an yellowish solid containing CA 4% t-BuOH ($^1$H NMR).

Step B: (5-{4-[3-Chloro-4-(3-fluoro-benzyloxy)-phenylamino]-quinazolin-6-yl}-furan-2-ylmethyl)-carbamic acid tert-butyl ester

[3-Chloro-4-(3-fluoro-benzyloxy)-phenyl]-(6-iodo-quinazolin-4-yl)-amine hydrochloride (0.913 g, 1.68 mmol) (from Step E, Example 1) is dissolved in DMF (20 ml) and the solution is degassed under nitrogen. The above solution is added over 10 hours to a heated (110° C.) degassed suspension of tricyclohexyl phosphine (0.475 g, 1.7 mmol), palladium dichloride (15.2 mg, 0.086 mmol), potassium acetate (0.35 g, 3.6 mmol), tetra n-butyl ammonium bromide (0.552 g, 2.15 mmol), and Furan-2-ylmethyl-carbamic acid tert-butyl ester (2.9 g, 15 mmol) in DMF (5 ml). Heating is continued for 9 hours after the end of addition. The reaction mixture is cooled, diluted with water and extracted with EtOAc. The combined organic extracts are dried ($Na_2SO_4$) and concentrated under reduced pressure. Flash chromatography on silica with 10-50% EtOAc:hexanes gradient elution yields 0.450 g (0.78 mmol, 46%) of the clean desired product.

Step C: [6-(5-Aminomethyl-furan-2-yl)-quinazolin-4-yl]-[3-chloro-4-(3-fluoro-benzyloxy)-phenyl]-amine.

(5-(4-[3-Chloro-4-(3-fluoro-benzyloxy)-phenylamino]-quinazolin-6-yl)-furan-2-ylmethyl)-carbamic acid tert-butyl ester (0.0218 g, 0.0379 mmol) is dissolved in DCM (2 ml) and TFA (2 ml) is added dropwise. The reaction mixture is stirred at room temperature for 1 hour. The solvent is removed under a nitrogen stream and to the residue are added consecutively saturated aqueous potassium carbonate solution and DCM. The resulting mixture is extracted with DCM containing 5% THF, the combined organic extracts are dried ($Na_2SO_4$) and concentrated under reduced pressure to yield 17.6 mg (0.037 mmol, 98%) of the clean desired product.

Step D: 1-(5-{4-[3-Chloro-4-(3-fluoro-benzyloxy)-phenylamino]-quinazolin-6-yl}-furan-2-ylmethyl)-2-phenyl-N-cyano isourea

[6-(5-Aminomethyl-furan-2-yl)-quinazolin-4-yl]-[3-chloro-4-(3-fluoro-benzyloxy)-phenyl]-amine (148 mg, 0.313 mmol) and diphenyl cyanocarbonimidate (83 mg, 0.348 mmol) are suspended in a 1:2 THF:i-PrOH mixture (9 ml), and stirred overnight at room temperature under a nitrogen atmosphere. The resulting suspension is used in the next reaction step without purification.

Step E: N-(5-{4-[3-Chloro-4-(3-fluoro-benzyloxy)-phenylamino]-quinazolin-6-yl}-furan-2-ylmethyl)-N'-cyano-morpholine-4-carboxamidine.

To one third of the crude product suspension from Step H is added morpholine (0.03 ml, 0.34 mmol) and the reaction mixture is heated for 2 hours at 80-90° C. in a sealed reaction vial. The reaction mixture is cooled, morpholine (0.05 ml, 0.57 mmol) is added, and the heating (80-90° C.) is continued for 1 hour. Concentration of the reaction mixture followed by flash column chromatography on silica with a 1:3:96 $Et_3N$:MeOH:DCM eluant yields 9.8 mg (0.016 mmol, 15% yield over steps I and J) of clean desired product. MS ESI (+) m/z 612 (M+1) detected; 1H NMR (400 MHz, DMSO-$d_6$) δ 8.88 (s, 1H), 8.76 (s, 1H), 8.56 (s, 1H), 8.18 (d, 1H), 8.03 (s, 1H), 7.90 (s, 1H), 7.82 (d, 1H), 7.75 (d, 1H), 7.47 (m, 1H), 7.29 (m, 3H), 7.18 (m, 1H), 7.07 (d, 1H), 6.55 (d, 1H), 5.27 (s, 2H), 4.62 (d, 2H), 3.63 (m, 2H), 3.51 (m, 2H)

EXAMPLE 5

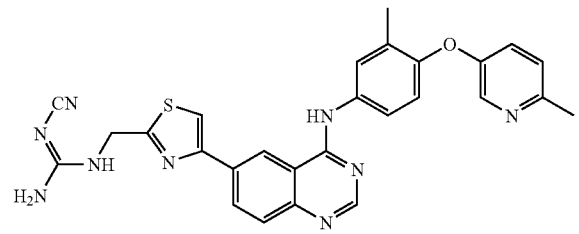

N-cyano-N'-(4-{4-[3-Methyl-4-(6-methyl-pyridin-3-yloxy)-phenylamino]-quinazolin-6-yl}-thiazol-2-ylmethyl)guanidine Step A: (4-Bromo-thiazol-2-yl)-methanol (modified procedure from Nicolaou et al., Bioorg. Med. Chem., 7 (1999), 665-697)

2,4-Dibromothiazole (4.31 g, 17.7 mmol) are dissolved in anhydrous diethyl ether (170 ml) and the solution is cooled to −78° C. (dry ice-acetone bath). n-Butyllithium (1.6 M in hexanes, 13 ml, 20.8 mmol) is added dropwise to the reaction mixture and the resulting solution is stirred at the same temperature for 30 minutes. Anhydrous DMF (ml, mmol) is then added at −78° C. and, after being stirred at the −78° C. for 30 minutes, the reaction mixture is warmed to room temperature over a period of 2 hours. Hexanes (300 ml), were added and the resulting mixture is passed through a short silica cake eluting with 30% EtOAc-hexanes. The solvents are evaporated to yield the crude aldehyde which is used directly in the next step.

To a solution of the above aldehyde in MeOH (80 ml) is added sodium borohydride (g, mmol), and the resulting mixture is stirred room temperature for hours. Hexanes (300 ml) are added and the mixture is passed through a short silica cake eluting with EtOAc. The crude alcohol is further purified by flash chromatography on silica with 20-50% EtOAc-hexanes as an eluant to yield g (mmol, %) of the pure desired product.

Step B: 2-Azidomethyl-4-bromo-thiazole.

(4-Bromo-thiazol-2-yl)-methanol (1.1 g, 5.7 mmol) in DMF (15 ml) is treated at room temperature under nitrogen atmosphere with trifluoromethanesulfonyl chloride (0.61 ml, 1 equivalent), and $Et_3N$ (0.8 ml, 1 equivalent). The reaction mixture is stirred for 3 hours at room temperature before the addition of sodium azide (1.11 g, 3 equivalents), followed by overnight stirring at the same temperature. The reaction mixture is diluted with water and extracted with DCM and diethyl ether. The combined organic extracts are dried ($MgSO_4$) and concentrated under reduced pressure to afford the crude product, which is used without purification in the next step.

Step C: (4-Bromo-thiazol-2-yl)-methylamine

Crude 2-Azidomethyl-4-bromo-thiazole from Step E is dissolved in a 1:3:2 THF:EtOH:$H_2O$ mixture, and treated with $PtO_2$ (wet, approximately 60 mg). The reaction flask is flushed with hydrogen from a balloon, and stirring under hydrogen atmosphere is continued for 3 hours. The reaction mixture is filtered through a Celite pad, diluted with DCM and diethyl ether, and dried ($Na_2SO_4$). Chromatography on silica pretreated with 1% $Et_3N$ in EtOAc with EtOAc-MeOH eluant affords 710 mg (3.68 mmol, 65%) of clean desired product.

Step D: (4-Bromo-thiazol-2-ylmethyl)-carbamic acid tert-butyl ester (4-Bromo-thiazol-2-yl)-methylamine (705.3 mg, 3.68 mmol) is dissolved in anhydrous DCM (15 ml) and $Boc_2O$ (898 mg, 4.13 mmol) is added. The reaction mixture is stirred at room temperature for 4 hours. Flash chromatography on silica with 0-20% EtOAc-hexanes affords 770 mg (2.64 mmol, 72%) of pure desired product.

Step E: (4-Trimethylstannyl-thiazol-2-ylmethyl)-carbamic acid tert-butyl ester (4-Bromo-thiazol-2-ylmethyl)-carbamic acid tert-butyl ester (0.46 g, 1.58 mmol) is added at room temperature to $Pd(PPh_3)_4$ (87 mg, 0.075 mmol) in anhydrous toluene (16 ml) under a nitrogen atmosphere. Hexamethylditin (5.0 g, 15.26 mmol) is added in one prtion and the resulting mixture is degassed under nitrogen. The reaction mixture is heated at 100° C. for 3 hours, then cooled to room temperature and loaded directly on a silica column pretreated with 1% $Et_3N$ in hexanes. Elution with 0-5% EtOAc-hexanes affords the crude product which is further purified by flash chromatography on silica with 0-30% EtOAc-hexanes gradient elution to yield 357.7 mg (0.950 mmol, 60%) of clean desired product.

Step F: (4-{4-[3-Methyl-4-(6-methyl-pyridin-3-yloxy)-phenylamino]quinazolin-6-yl}-thiazol-2-ylmethyl)-carbamic acid ter-butyl ester (4-Trimethylstannyl-thiazol-2-ylmethyl)-carbamic acid tert-butyl ester (191 mg, 0.507 mmol) and [3-Methyl-4-(6-methyl-pyridin-3-yloxy)-phenyl]-(6-iodo-quinazolin-4-yl)-amine hydrochloride (0.251 g, 0.478 mmol) (from Step C, Example 3) are dissolved in anhydrous DMF under a nitrogen atmosphere. Hunig's base (0.44 ml, 2.53 mmol), and $PdCl_2(PPh_3)_2$ are added to the reaction mixture at room temperature. The reaction mixture is degassed and heated at 100° C. overnight. After cooling to room temperature the reaction mixture is diluted with with water and thoroughly extracted with EtOAc and DCM. The combined organic extracts are dried ($Na_2SO_4$) and concentrated under reduced pressure. Flash chromatography on silica with EtOAc-MeOH as an eluant affords 81 mg (0.14 mmol, 28%) of clean desired product.

Step G: [6-(2-Aminomethyl-thiazol-4-yl)-quinazolin-4-yl]-[3-methyl-4-(6-methyl-pyridin-3-yloxy)-phenyl]-amine (4-{4-[3-Methyl-4-(6-methyl-pyridin-3-yloxy)-phenylamino]quinazolin-6-yl}-thiazol-2-ylmethyl)-carbamic acid ter-butyl ester (81 mg, 0.14 mmol) is treated with concentrated aqueous hydrochloric acid (0.5 ml) in EtOAc (6 ml). Reaction progress is followed by LC/MS. Upon reaction completion saturated aqueous potassium carbonate solution is added, the reaction mixture is diluted with water and thoroughly extracted with DCM and EtOAc. The combined organic extracts are dried ($Na_2SO_4$) and concentrated under reduced pressure to yield 45 mg (0.095 mmol, 68%) of clean desired product.

Step H: 1-(4-{4-[3-Methyl-4-(6-methyl-pyridin-3-yloxy)-phenylamino]quinazolin-6-yl}-thiazol-2-ylmethyl)-2-phenyl-N-cyano isourea

[6-(2-Aminomethyl-thiazol-4-yl)-quinazolin-4-yl]-[3-methyl-4-(6-methyl-pyridin-3-yloxy)-phenyl]-amine (45 mg, 0.095 mmol) is dissolved in a 1:2 i-PrOH:THF mixture (6 ml). Diphenyl cyanocarbonimidate (28 mg, 0.12 mmol) is added and the reaction mixture is stirred overnight at room temperature under a nitrogen atmosphere. To drive the reaction to completion diphenyl cyanocarbonimidate (20 mg, 0.09 mmol) is added to reaction mixture, which is stirred at room temperature for another 4 hours. The reaction mixture is then concentrated and purified by flash column chromatography on silica eith MeOH-EtOAc as an eluant. The yield of pure desired product is 42 mg (0.07 mmol, 74%).

Step I: N-cyano-N'-(4-{4-[3-Methyl-4-(6-methyl-pyridin-3-yloxy)-phenylamino]-quinazolin-6-yl}-thiazol-2-ylmethyl) guanidine 1-(4-{4-[3-Methyl-4-(6-methyl-pyridin-3-yloxy)-phenylamino]quinazolin-6-yl}-thiazol-2-ylmethyl)-2-phenyl-N-cyano isourea (8.4 mg, 0.014 mmol) is dissolved in a 1:1 mixture of THF:i-PrOH (2 ml), and treated with 2.0 M ammonia solution in MeOH (0.1 ml). The reaction mixture is heated at 80 C in a sealed reaction vial until the reaction is complete by LC/MS. Flash chromatography on silica with MeOH-EtOAc as an eluant affords 5.7 mg (0.011 mmol, 79%) of pure desired product. MS ESI (+) m/z 522 (M+1) detected; $^1$H NMR (400 MHz, DMSO-$d_6$) δ 9.08 (s, 1H), 8.57 (s, 1H), 7.83 (m, 2H), 7.72 (d, 1H), 7.63 (bs, 1H), 7.25 (m, 2H), 7.14 (bs, 2H), 6.98 (d, 2H), 4.70 (m, 2H), 2.45 (s, 3H), 2.23 (s, 3H).

EXAMPLE 6

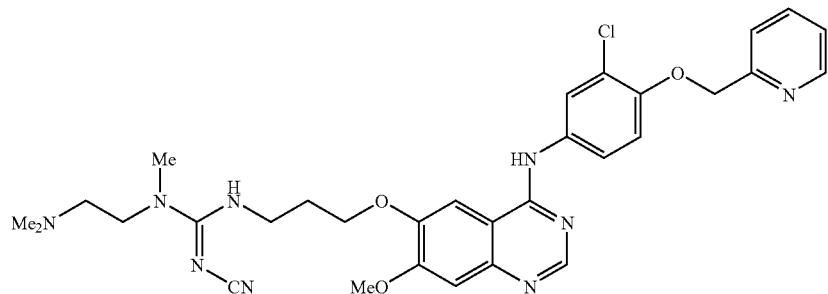

N-(3-{4-[3-Chloro-4-(pyridin-2-ylmethoxy)-phenylamino]-7-methoxy-quinazolin-6-yloxy}-propyl)-N'-cyano-N"-(2-dimethylamino-ethyl)-N"-methylguanidine Step A: 2-(2-Chloro-4-nitro-phenoxymethyl)-pyridine
Sodium hydride (95%, 0.935 g, 37 mmol) is suspended in dry DMF (20 ml) under a nitrogen atmosphere and the resulting mixture is cooled in ice water. To above suspension is added dropwise over 15 minutes pyridin-2-yl-methanol (3.42 g, 31.3 mmol) in dry DMF (20 mL). Next, to the cold reaction mixture is added dropwise over 20 minutes a solution of 2-Chloro-1-fluoro-4-nitro-benzene (5 g, 28.5 mmol) in dry DMF (20 ml). Upon the end of addition the cold bath is removed and the reaction mixture is stirred for another 36 hours. Water (80 mL) was added slowly to the reaction mixture, and a yellow precipitate resulted. The resultant solid is isolated by suction filtration, washed with water (80 ml), and air dried to yield 7.52 g (28.5 mmol, 100%) of the clean desired material as a yellow powder.

Step B: 3-Chloro-4-(pyridin-2-ylmethoxy)-phenylamine 2-(2-Chloro-4-nitro-phenoxymethyl)-pyridine (2.4 g, 9.07 mmol) is suspended in MeOH (30 ml) and treated wet 5% Pt/C (Degussa type, Aldrich, 0.8 g). The flask is flushed with hydrogen gas from a balloon and the reaction mixture is stirred under hydrogen atmosphere until reaction is complete by TLC (ca 2 hours). The reaction mixture is filtered through a Celite plug and the solvent is removed under reduced pressure. The crude product is redissolved in DCM, dried ($MgSO_4$) and concentrated to yield 1.7 g (7.23 mmol, 80%) of the desired product.

Step C: 2-Amino-5-hydroxy-4-methoxy-benzoic acid

5-Hydroxy-4-methoxy-2-nitro-benzoic acid (18 g, 84.51 mmol, *J. Indian Chem. Soc.* 1970, 70, 925) is suspended in MeOH (1 L) and treated $PtO_2$ (100 mg). The flask is flushed with hydrogen gas and the reaction mixture is stirred under hydrogen atmosphere (45 psi) for 4 hours. The reaction mixture is filtered through a celite plug and the solvent is removed under reduced pressure. The crude product is redissolved in DCM, dried ($MgSO_4$) and concentrated to yield 15.06 g (82.3 mmol, 97%) of the desired product.

Step D: 7-Methoxy-quinazoline-4,6-diol

Piperidine (3 mL, 31 mmol) was added to a mixture of 2-Amino-5-hydroxy-4-methoxy-benzoic acid (8.1 g, 44.26 mmol) and triazine (5.38 g, 66.4 mmol) in MeOH (60 mL). The reaction was then heated to reflux and stir for 6 hours. The reaction was cool to 0oC. The product was isolated by filtration and washed with cold MeOH to give 6.37 g (33.2 mmol, 75%) of desired product.

Step E: Acetic acid 4-hydroxy-7-methoxy-quinazolin-6-yl ester

A mixture of 7-Methoxy-quinazoline-4,6-diol (6.2 g, 32.3 mmol), $Ac_2O$ (100 mL) and pyridine (10 mL) was heat to 100° C., and stirred for 3 hours. The reaction was then cooled to room temperature and poured to ice water (300 mL). The product was isolated by filtration, washed with water (200 mL) and dried to give 7.61 g (32.4 mmol, 100%) of desired product.

Step F: Acetic acid 4-chloro-7-methoxy-quinazolin-6-yl ester

To a stirred solution of anhydrous DMF (4.5 mL) in DCE (20 mL), cooled in an ice-water bath, is added dropwise under nitrogen a solution of oxalyl chloride (7.9 ml, 90 mmol) in DCE (40 mL). A white precipitate forms during the addition. After the end of addition the cold bath is removed and the reaction mixture is stirred at room temperature for 5 min. Acetic acid 4-hydroxy-7-methoxy-quinazolin-6-yl ester (6.5 g, 27.8 mmol) is added in portions via scoopula under nitrogen flow and the mixture is heated immediately to reflux. Heating is continued for 3 hours, followed by cooling to room temperature. The reaction mixture is poured into excess ice: water mixture (100 mL) and extracted with DCM (500 mL). The aqueous layer is further extracted with DCM (2×50 mL). The combined organic extracts are dried ($Na_2SO_4$) and concentrated under reduced pressure to yield 5.63 g (22.34 mmol, 80%) of desired product as a tan solid.

Step G: 4-[3-Chloro-4-(pyridin-2-ylmethoxy)-phenylamino]-7-methoxy-quinazolin-6-ol 3-Chloro-4-(pyridin-2-ylmethoxy)-phenylamine (3.9 g, 16.62 mmol) and acetic acid 4-chloro-7-methoxy-quinazolin-6-yl ester (4.62 g, 18.28 mmol) were dissolved in a 1:1 mixture of DCE:t-BuOH (50 mL). The reaction mixture was refluxed for 19 hours and then cooled to room temp. Solvent was removed via rotovap. The crude residue was then suspended in MeOH (80 mL) and $NH_4OH$ (8 mL, 30% in water) was added to the mixture. Stir for 15 hours at room temp. The reaction was heated to 100° C. and stirred for 1 hour. Cool to 0° C. and product was isolated by filtration and washed with cold MeOH to give 5 g (12.2 mmol, 67% over two steps) of desired product.

Step H: (3-{4-[3-Chloro-4-(pyridin-2-ylmethoxy)-phenylamino]-7-methoxy-quinazolin-6-yloxy}-propyl)-carbamic acid tert-butyl ester CsOH monohydrate (0.452 g, 2.69 mmol) was added to a mixture of 4-[3-Chloro-4-(pyridin-2-ylmethoxy)-phenylamino]-7-methoxy-quinazolin-6-ol (1 g, 2.45 mmol), (3-bromo-propyl)-carbamic acid tert-butyl ester (0.64 g, 2.69 mmol), tetrabutylammonium iodide (5 mg) and 4 Å molecular sieves (2 g) in DMF (10 mL) at room temp. Stir for 3 hours. The reaction mixture was then filtered through celite and washed with EtOAc (30 mL). The organic solution was washed with water (20 mL) and concentrated. FLC (10:1 EtOAc:Hexanes) provided desired product (1.02 g, 73.7%).

Step I: [6-(3-Amino-propoxy)-7-methoxy-quinazolin-4-yl]-[3-chloro-4-(pyridin-2-ylmethoxy)-phenyl]-amine TFA (3 mL) was added drop wise to a suspension of (3-{4-[3-Chloro-4-(pyridin-2-ylmethoxy)-phenylamino]-7-methoxy-quinazolin-6-yloxy}-propyl)-carbamic acid tert-butyl ester (0.9 g, 1.59 mmol) in DCM (3 mL). Stir for 1 hour and the reaction mixture was diluted with DCM (20 ml) and sat. NaHCO$_3$ (20 mL). Phases were separated and organic layer was extracted with DCM (20 mL). Organic layers were combined, dried (Na$_2$SO$_4$), and concentrated to give 0.7 g (95%) of desired product.

Step J: N-(3-{4-[3-Chloro-4-(pyridin-2-ylmethoxy)-phenylamino]-7-methoxy-quinazolin-6-yloxy}-propyl)-N'-cyano-N''-(2-dimethylamino-ethyl)-N'''-methylguanidine The primary amine was functionalized to the corresponding N-cyanoguanidine in the similar fashion as described in the previous examples. MS ESI (+) m/z 618 (M+1) detected; $^1$H NMR (400 MHz, deuterated DMSO) δ 9.4 (s, 1H), 8.6 (d, J=4 Hz, 1H), 8.4 (s, 1H), 8.0-7.8 (m, 4H), 7.7 (dd, J=8,2 Hz, 1H), 7.6 (d, J=8 Hz, 1H), 7.3 (t, J=7 Hz, 1H), 7.2 (d, J=9 Hz, 1H), 7.17 (s, 1H), 5.2 (s, 2 H), 4.18 (t, J=6 Hz, 2H), 3.91 (s, 3H), 3.6-3.4 (m, 4H), 3.39 (t, J=6 Hz, 2H), 3.27 (q, J=6 Hz, 2H), 2.92 (s, 3H), 2.1 (s, 6H), 2.06 (m, 2H).

EXAMPLE 7

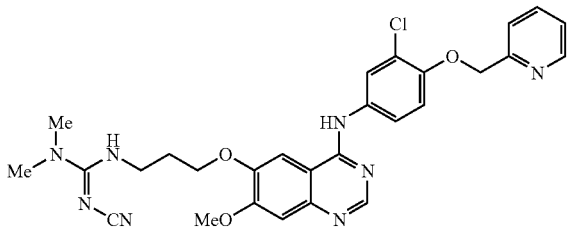

N-(3-{4-[3-Chloro-4-(pyridin-2-ylmethoxy)-phenylamino]-7-methoxy-quinazolin-6-yloxy}-propyl)-N'-cyano-N'',N''-dimethylguanidine Prepared similarly as N'-(3-{4-[3-Chloro-4-(pyridin-2-ylmethoxy)-phenylamino]-7-methoxy-quinazolin-6-yloxy}-propyl)-N-(2-dimethylamino-ethyl)-N-methyl-N-cyanoguanidine.

MS ESI (+) m/z 561 (M+1) detected; $^1$H NMR (400 MHz, deuterated DMSO) δ 9.4 (s, 1H), 8.6 (d, J=4 Hz, 1H), 8.4 (s, 1H), 7.95 (d, J=3 Hz, 1H), 7.87 (td, J=8,1 Hz, 1H), 7.81 (s, 1H), 7.67 (dd, J=8,2 Hz, 1H), 7.57 (d, J=8 Hz, 1H), 7.35 (dd, J=7,5 Hz, 1H), 7.25 (d, J=9 Hz, 1H), 7.17 (s, 1H), 7.1 (t, J=6 Hz, 1H), 5.2 (s, 2 H), 4.18 (t, J=6 Hz, 2H), 3.91 (s, 3H), 3.5 (q, J=7 Hz, 2H), 2.94 (s, 6H), 2.1 (m, 2H).

EXAMPLE 8

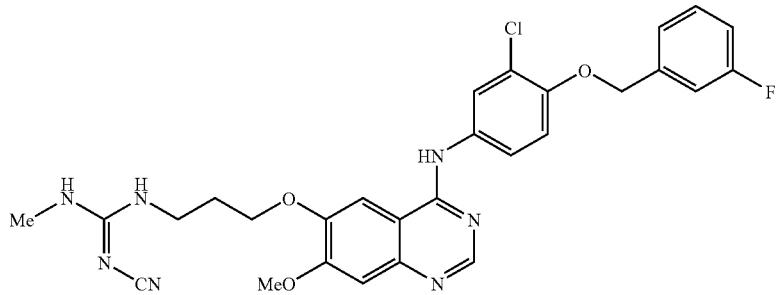

N-(3-{4-[3-Chloro-4-(3-fluoro-benzyloxy)-phenylamino]-7-methoxy-quinazolin-6-yloxy}-propyl)-N'-cyano-N''-methylguanidine Prepared similarly as N'-(3-{4-[3-Chloro-4-(pyridin-2-ylmethoxy)-phenylamino]-7-methoxy-quinazolin-6-yloxy}-propyl)-N-(2-dimethylamino-ethyl)-N-methyl-N-cyanoguanidine, except that 3-Chloro-4-(3-fluoro-benzyloxy)-phenylamine in stead of 3-Chloro-4-(pyridin-2-ylmethoxy)-phenylamine was used in Step G in Example 6. MS ESI (+) m/z 539 (M+1) detected; $^1$H NMR (400 MHz, deuterated DMSO) δ 9.43 (s, 1H), 8.46 (s, 1H), 7.96(d, J=3 Hz, 1H), 7.82 (s, 1H), 7.7 (dd, J=9,2 Hz, 1H), 7.5 (q, J=6 Hz, 1H), 7.33 (d, J=8 Hz, 1H), 7.31 (d, J=9 Hz, 1H), 7.27 (d, J=9 Hz, 1H), 7.2-7.1 (m, 2H), 7.03 (m, 1H), 7.69 (m, 1H), 5.2 (s, 2 H), 4.18 (t, J=6 Hz, 2H), 3.94 (s, 3H), 2.68 (d, J=6 Hz, 3H), 2.05 (m, 2H).

EXAMPLE 9

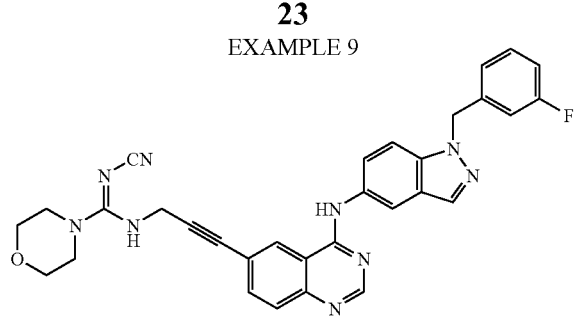

N-cyano-N'-(3-{4-[1-(3-Fluoro-benzyl)-1 H-indazol-5-ylamino]-quinazolin-6-yl}-prop-2-ynyl)-morpholine-4-carboxamidine Step A: 1-(3-Fluoro-benzyl)-5-nitro-1 H-indazole A modified procedure from WO 99/35146, p. 61was followed. 5-nitroindazole (3.915 g, 24 mmol) treated with potassium carbonate (3.65 g, 1.1 equiv.), and 3-fluorobenzyl bromide (5 g, 1.1 equiv.) in 41 ml of dry DMF under $N_2$. Reaction mixture is stirred at 75° C. for 4 hours. The crude product (yellow solid, 5.536 g) is isolated as in the reference procedure. Acetone (26 ml) is added to the crude product, and the insoluble solids are filtered off. To filtered solution is added water dropwise (12 ml) upon which an oil forms. The mixture is store in freezer at −20 C for 15 min, upon which the oil solidifies and remains solid after warming to r.t. Chromatography of the solid (silica, 0-10% EtOAc/hexanes) afforded 2.49 g of high Rf material (1-H regioisomer, 9.2 mmol, 38%), 0.7 g of the low Rf material (2-H isomer, 11%) and mixed fractions (0.71 g, 3%).

Step B: 1-(3-Fluoro-benzyl)-1 H-indazol-5-ylamine

Follow modified procedure from WO 99/35146. 1-(3-Fluoro-benzyl)-5-nitro-1H-indazole (2.49 g, 9.2 mmol) is suspended in 40 ml absolute EtOH and Pt/C (5%, wet, 150 mg) is added. The reaction mixture is stirred and heated at 60° C. under a hydrogen atmosphere (balloon). Roughly 4 hours into the reaction LC/MS reveals the formation of substantial amounts of product. The mixture is filtered through Celite and concentrated under reduced pressure. Yield: 2.01 g (90.8%) of a white solid.

Step C: [1-(3-Fluoro-benzyl)-1 H-indazol-5-yl]-(6-iodo-quinazolin-4-yl)-amine hydrochloride Follow general procedure from Example 1, step E. 4-chloro-6-iodoquinazoline (1.18 g, 4.06 mmol) is mixed with 1-(3-Fluoro-benzyl)-1H-indazol-5-ylamine (1.09 g, 4.52 mmol), and a mixture of DCE (10 ml) and t-BuOH (10 ml) is added. The mixture is heated at 90° C. (oil bath temperature) for 8 hours. At 5 hours of heating LC/MS reveals substantial amount of product. Yield is 1.35 g (56%).

Step D: (3-{4-[1-(3-Fluoro-benzyl)-1H-indazol-5-ylamino]-quinazolin-6-yl}-prop-2-ynyl)-carbamic acid tert-butyl ester

[1-(3-Fluoro-benzyl)-1 H-indazol-5-yl]-(6-iodo-quinazolin-4-yl)-amine hydrochloride (0.334 g, 0.628 mmol) and Prop-2-ynyl-carbamic acid tert-butyl ester (113 mg, 1.16 equiv.) is treated with i-$Pr_2$NH (2 equiv.) in dry THF (4 ml) under $N_2$. $Pd(PPh_3)_4$ (25 mg, 0.0356 mmol, 5.7 mol %) and solid CuI (5 mol %) are added next, and the mixture is stirred at r.t. for 3 hours. Workup: THF is removed under reduced pressure and DCM (10 ml) is added. The organic layer is washed with sat. aq. NH4Cl solution and brine, dried and concentrated. Chromatography on silica (EtOAc/hexanes) affords the desired pure product (293 mg, 89%).

Step E: [6-(3-Amino-prop-1-ynyl)-quinazolin-4-yl]-[1-(3-fluoro-benzyl)-1H-indazol-5-yl]-amine (3-{4-[1-(3-Fluoro-benzyl)-1H-indazol-5-ylamino]-quinazolin-6-yl}-prop-2-ynyl)-carbamic acid tert-butyl ester (285 mg, 0.545 mmol) is suspended in DCM (6 ml) and TFA (6 ml) is added dropwise. The reaction is stirred at r.t. for 2 hours. The solvents are removed in a $N_2$ stream, DCM (10 ml) is added, and the organic layer is treated with sat. aq. $NaHCO_3$ and brine, dried, and concentrated to afford the pure product (197.6 mg, 86%).

Step F: 1-(3-{4-[1-(3-Fluoro-benzyl)-1H-indazol-5-ylamino]-quinazolin-6-yl}-prop-2-ynyl)-2-phenyl-3-cyano-isourea

[6-(3-Amino-prop-1-ynyl)-quinazolin-4-yl]-[1-(3-fluoro-benzyl)-1H-indazol-5-yl]-amine (280 mg, 0.663 mmol) is treated with diphenyl cyanocarbonimidate (163 mg, 1.031 equiv.) in a mixture of i-PrOH (12 ml) and THF (4 ml). Stir mixture overnight, then concentrate to dryness and chromatograph on silica (EtOAc/hexanes) to obtain 186.3 mg (49.6%) of pure desired product.

Step G: N-cyano-N'-(3-{4-[1-(3-Fluoro-benzyl)-1H-indazol-5-ylamino]-quinazolin-6-yl}-prop-2-ynyl)-morpholine-4-carboxamidine Material from step F (9 mg, 0.016 mmol) is placed in a reaction vial and dissolved in 2 ml of a 1:1 THF:i-PrOH mixture. Morpholine (0.08 mmol) is added at r.t, and the sealed vial is heated in an oil bath at 80° C. Reaction progress at 80° C. is followed by LC/MS, and the reaction is stopped after reaching 90% conversion (3 hours). Chromatography of the crude on silica (MeOH/EtOAc) affords pure desired product (1.8 mg, 20%). MS ESI (+) m/z 560 (M+1) detected; $^1$H NMR (400 MHz, deuterated acetone containing 10% deuterated methanol) δ 8.58 (s, 1H), 8.55 (s, 1H), 8.39 (s, 1H), 8.11 (s, 1H), 7.84-7.76 (m, 4H), 7.65 (d, 1H), 7.37 (q, 1H), 7.12 (d, 1H), 7.04 (m, 2H).

EXAMPLE 10

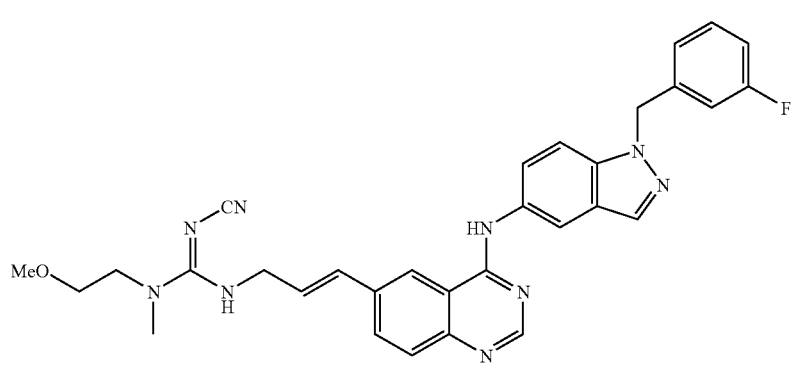

N-cyano-N'-(3-{4-[1-(3-Fluoro-benzyl)-1H-indazol-5-ylamino]-quinazolin-6-yl}-allyl)-N''-(2-methoxyethyl)-N''-methylguanidine Step A: (3-{4-[1-(3-Fluoro-benzyl)-1H-indazol-5-ylamino]-quinazolin-6-yl}-allyl)-carbamic acid tert-butyl ester To a cold (ice-water bath) Red-Al (0.52 ml, 65% wt solution in toluene, 1.74 mmol) solution in THF (3 ml) added a solution of the s.m. alkyne (350 mg, 0.670 mmol) in THF (4 ml). Stir at 0° C. for 2.5 hours. Reaction is quenched with 10% aqueous potassium carbonate solution and diluted with distilled water. The mixture is extensively extracted with EtOAc and DCM, dried, and concentrated. Yield after chromatography (silica, EtOAc/hexanes) is 215.4 mg of pure product (61%).

Step B: [6-(3-Amino-propenyl)-quinazolin-4-yl]-[1-(3-fluoro-benzyl)-1H-indazol-5-yl]-amine The desired product was obtained through a procedure analogous to the one outlined in Example 9, step E.

Step C: 1-(3-{4-[1-(3-Fluoro-benzyl)-1H-indazol-5-ylamino]-quinazolin-6-yl}-allyl)-2-phenyl-3-cyano-isourea The desired material was obtained through a procedure analogous to the one outlined in Example 9, step F.

Step D: N-cyano-N'-(3-{4-[1-(3-Fluoro-benzyl)-1H-indazol-5-ylamino]-quinazolin-6-yl}-allyl)-N''-(2-methoxyethyl)-N''-methylguanidine Material from step C (10 mg, 0.0168 mmol) dissolved in 2 ml of a 1:1 THF:i-PrOH mixture and treated with 10 equivalents of MeHNCH$_2$CH$_2$OMe and heat to 80° C. The reaction was monitored by LC/MS. Up to five additional equivalents of amine can be added when necessary to drive the reaction forward. The reaction was stopped (by cooling vial to room temperature) when the conversion exceeded 60% (80-90% conversion is usually attained before end of the reaction). Chromatography of the crude on silica (0-10% MeOH-EtOAc) followed by preparative TLC (silica, MeOH/EtOAc) afforded 3.2 mg (34%) of the desired product. MS ESI (+) m/z 564 (M+1) detected; $^1$H NMR (400 MHz, deuterated acetone) δ 9.34 (s, 1H), 8.56 (s, 1H), 8.45 (d, 1H), 8.44 (m, 1H), 8.10 (s, 1H), 7.97 (dd, 1H), 7.77 (m, 2H), 7.64 (d, 1H), 7.37 (m, 1H), 7.12 (d, 1H), 7.05 (m, 2H), 6.79 (m, 2H), 6.55 (dt, 1H), 5.73 (s, 2H), 4.31 (m, 2H), 3.36 (s, 3H), 3.12 (s, 3H), 3.63 (m, 4H).

EXAMPLE 11

The extent to which the compounds of the present invention modulate ErbB kinase activity can be determined using the following enzyme-linked immunosorbent assay (ELISA), which employs a microtiter plate coated with a protein tyrosine kinase specific polymer substrate. The phosphorylation reaction is performed on poly-Glu-Tyr 4:1 (PGT) coated microtiter plates in the presence on Mg$^{++}$, ATP and EGFR. The phosphorylated polymer substrate is detected with a phosphotyrosine specific monoclonal antibody conjugated to horseradish peroxidase (HRP). Chromogenic substrate (TMB) color is quantitiated by spectrophotometry.

The assay is performed in a 96-well microtiter plate (Immunlon 4, available from Dynex). To prepare the plate, 100 µL of 0.25 mg/mL Poly (Glu,Tyr) 4:1 Sodium Salt (available from Sigma, Catalog Number P0275) in phosphate buffered saline (PBS) is added to each well and the plates are sealed. Following incubation overnight at ambient temperature, this coating solution is removed and the plates are washed three times with 300 µL of 0.1% Tween 20 (available from Sigma, Catalog Number P2287) in PBS. If not using immediately, the coated microtiter plates may be stored at 2-8° C. with 150 µL of 0.1% Tween 20 in PBS in each well.

The compound to be tested is dissolved in DMSO at an initial concentration of 1.0 mM. This initial concentration is diluted 1:25 in DMSO, and the resulting solution is further serially diluted 1:5 eight times in DMSO. To 10 µL of the initial concentration and each dilution are added 240 µL Reaction Buffer (50 mM HEPES, 125 mM NaCl, 24 mM MgCl$_2$, 0.1 mM Na$_3$VO$_4$ (boiled at pH 10 until colorless—approximately 10 minutes—and cooled prior to use), pH 7.3, filtered through a 0.2 micron filter). 25 µL of each compound solution (4% DMSO in Reaction Buffer for control) is placed in a separate microtiter plate well, along with 50 µL Reaction Buffer +ATP (15 µL 10 of mM ATP added to 5 mL Reaction Buffer) and 25 µL Reaction Buffer into which a catalytic amount of baculovirus ErbB2 has been added. The plate is then covered and incubated for 30 minutes at room temperature, after which time all liquid is aspirated from each well. The plate is washed three times with 300 µL of 0.1% Tween in PBS. Residual wash solution is removed by inverting the plate and blotting on a paper towel.

To each well is then added 100 µL of PBS containing 3% bovine serum albumin (protease-free, IgG-free, Jackson Catalog Number 001-000-162), 0.05% Tween 20 and 0.2 µg/mL anti-phosphotyrosine horseradisn peroxidase (available from Zymed, Laboratories, Inc., Catalog Number 03-7720). The plate is covered and incubated for 30 minutes at room temperature, after which time all liquid is aspirated from each well. The plate is washed three times with 300 µL of 0.1% Tween in PBS. Residual wash solution is removed by inverting the plate and blotting on a paper towel. To each well is then added 100 µL of TMB peroxidase substrate system (KPL Catalog Number 50-76-00), and the plate is allowed to incubate for 25 minutes at room temperature, at which time the reaction is stopped by the addition of 100 µL of 1M phosphoric acid to each well. The plate is tapped gently to ensure mixing.

Within about thirty minutes after the reaction is stopped, the optical density at 450 nm of each well is determined using a microtiter plate reader. A dose response curve is generated by plotting optical density versus compound concentration. IC$_{50}$ is calculated from this curve using methods known in the art.

With this assay, the following IC$_{50}$ values of selected compounds of the present invention set forth in Table 1 below were determined.

TABLE 1

| Example # | IC$_{50}$ (nm) |
|---|---|
| 1 | 85 |
| 2 | 410 |
| 3 | 8 |
| 4 | 13 |
| 5 | 31 |
| 6 | 14 |
| 7 | 33 |
| 8 | 40 |
| 9 | 12 |
| 10 | 17 |

Obviously, numerous modifications and variations of the present invention are possible in light of the above teachings. It is therefore to be understood that, within the scope of the appended claims, the invention may be practiced otherwise than as specifically described herein.

What is claimed is:

1. A compound, including enantiomers, diastereoisomers, tautomers, and pharmaceutically acceptable salts, having the following formula (I):

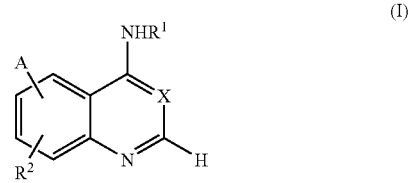

wherein at least one of the positions 6 or 7 of the quinazoline ring must be substituted by a group A, and the remaining positions on the quinazoline ring may be optionally substituted by up to three $R^2$ groups; wherein X is N;

$R^1$ is

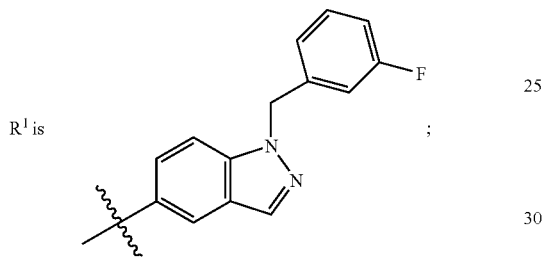

;

$R^7$ and $R^{10}$ independently represent hydrogen or $C_{1-6}$ alkyl, or $R^7$ and $R^{10}$ together with the atom to which they are attached form a 4 to 10 membered carbocyclic, heteroaryl or heterocyclic ring, each of which is optionally substituted with up to three groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

$R^8$ represents trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, where each alkyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

$R^9$ represents hydrogen, trifluoromethyl, $C_1$-$C_{10}$ alkyl, $(CH_2)_n C_3$-$C_{10}$ cycloalkyl, aryl, arylalkyl, heteroaryl, heteroarylalkyl, heterocyclyl or heterocyclylalkyl, where each alkyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, aryl, heteroaryl, arylalkyl, heteroarylalkyl, heterocyclyl and heterocyclylalkyl, where n=0 or 4, or when a substituent is —$SO_2NR^9R^7$, —$NR^7C(O)R^9$, —$C(O)NR^7R^9$, —$NR^7R^9$, or —$NR^{10}C(O)NR^7R^9$, then the $R^7$ and $R^9$ of these substituents together with the atom to which they are each attached optionally form a 4 to 10 membered carbo cyclic, heteroaryl or heterocyclic ring, each of which is optionally substituted with up to three groups independently selected from halogen, cyano, nitro, trifluoromethyl, difluoromethoxy, trifluoromethoxy, azido, aryl, heteroaryl, arylalkyl, heteroarylalkyl, heterocyclyl and heterocyclylalkyl;

$R^{13}$ represents trifluoromethyl, difluoromethyl, $C_1$-$C_{10}$ alkyl, $C_3$-$C_{10}$ alkenyl, $C_3$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, where each of the above alkyl, alkenyl, alkynyl, cycloalkyl, aryl, heteroaryl and heterocyclyl portions of $R^{13}$ are optionally substituted with one to five groups independently selected from oxo, halogen, cyano, nitro, trifluoromethyl, difluoromethoxy, trifluoromethoxy, azido, —$NR^7SO_2R^8$, —$SO_2NR^9R^7$, —$C(O)R^9$, —$C(O)O R^9$, —$OC(O)R^9$, —$NR^7C(O)O R^8$, —$NR^7C(O)R^9$, —$C(O)NR^7R^9$, —$NR^7R^9$, —$NR^{10}C(O)NR^7R^9$, —$NR^{10}C(NCN)NR^7R^9$, —$OR^9$, aryl, arylalkyl, heteroaryl, heteroarylalkyl, heterocyclyl and heterocyclylalkyl; where $R^7$, $R^8$, $R^9$ and $R^{10}$ are the same as $R^7$, $R^8$, $R^9$ and $R^{10}$ defined above;

$R^2$ represents hydrogen, halogen, cyano, nitro, trifluoromethyl, difluoromethyl, trifluoromethoxy, —OMe, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —$NR^7SO_2R^8$,— $SO_2NR^9R^7$, —$C(O)R^9$, —$C(O)OR^9$, —$OC(O)R^9$, —$OC(O)R^9$, —$NR^7C(O)OR^8$, —$NR^7C(O)CR^9$,—$C(O)NR^7R^9$, —$NR^7R^9$, —$NR^{10}C(O)NR^7R^9$, —$NR^{10}C(NCN)NR^7R^9$,—$OR^9$, —$S(O)R^{13}$, —$SO_2R^{13}$, aryl, arylalkyl, heteroaryl, heteroarylalkyl, heterocyclyl and heterocyclylalkyl, and where $R^7$, $R^8$, $R^9$, $R^{10}$ and $R^{13}$ are the same as $R^7$, $R^8$, $R^9$, $R^{10}$ and $R^{13}$ as defined above;

A is represented by the following formula (II):

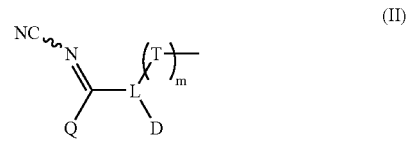

wherein

T represents $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl; where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —$NR^7SO_2R^8$, —$SO_2NR^9R^7$, —$C(O)R^9$, —$C(O)OR^9$, —$OC(O)R^9$, —$NR^7C(O)OR^8$, —$NR^7C(O)R^9$, —$C(O)NR^7R^9$, —$NR^7R^9$, —$NR^{10}C(O)NR^7R^9$, —$NR^{10}C(NCN)NR^7R^9$, —$OR^9$, —$S(O)R^{13}$, —$SO_2R^{13}$, aryl, arylalkyl, heteroaryl, heteroarylalkyl, heterocyclyl and heterocyclylalkyl, where $R^7$, $R^8$, $R^9$, $R^{10}$ and $R^{13}$ are the same as $R^7$, $R^8$, $R^9$, $R^{10}$ and $R^{13}$ as defined above;

T may optionally contain one or more heteroatoms, which heteroatoms may be further substituted or oxidized; and m is an integer from 0 to 1;

L is a nitrogen atom or a $CR^4$ group where $R^4$ represents hydrogen, trifluoromethyl, difluoromethyl, trifluoromethoxy, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —$NR^7SO_2R^8$, —$SO_2NR^9R^7$, —$C(O)R^9$, —$C(O)OR^9$, —$OC(O)R^9$, —$NR^7C(O)OR^8$, —$NR^7C(O)CR^9$, —$C(O)NR^7R^9$, —$NR^7R^9$, —$NR^{10}C(O)NR^7R^9$, —$NR^{10}C(NCN)NR^7R^9$, —$OR^9$, —$S(O)R^{13}$, —$SO_2R^{13}$, aryl, arylalkyl, heteroaryl, heteroarylalkyl, heterocyclyl and heterocyclylalkyl; where $R^7$, $R^8$, $R^9$, $R^{10}$ and $R^{13}$ are the same as $R^7$, $R^8$, $R^9$, $R^{10}$ and $R^{13}$ defined above;

Q is selected from $CR^3R^{11}R^{12}$ and $NR^{11}R^{12}$, where $R^3$ is the same as $R^2$ defined above and $R^{11}$ and $R^{12}$ independently represent hydrogen, trifluoromethyl, difluoromethyl, trifluoromethoxy, $C_1$-$C_{10}$ alkyl, $C_2$-$C_{10}$ alkenyl, $C_2$-$C_{10}$ alkynyl, $C_3$-$C_{10}$ cycloalkyl, $C^3$-$C_{10}$ cycloalkylalkyl, aryl, arylalkyl, heteroaryl, heteroarylalkyl, heterocyclyl, heterocyclylalkyl, —$NR^7SO_2R^8$, —$SO_2NR^9R^7$, —$C(O)R^9$, —$C(O)OR^9$, —$OC(O)R^9$, —$NR^7C(O)OR^8$, —$NR^7C(O)R^9$, —$C(O)NR^7R^9$, —$NR^7R^9$, —$NR^{10}(O)NR^7R^9$, —$OR^9$, —$S(O)R^{13}$ or —$SO_2R^{13}$, where each $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl and heterocyclylalkyl portion may be optionally substituted with up to five groups independently selected from oxo, halogen, cyano, nitro, trifluoromethyl, difluoromethoxy, trifluoromethoxy, azido, —$NR^7SO_2R^8$, —$SO_2NR^9R^7$, —$C(O)R^9$, —$C(O)OR^9$, —$OC(O)R^9$, —$NR^7C(O)OR^8$, —$NR^7C(O)R^9$, —$C(O)NR^7R^9$, —$NR^7R^9$, —$NR^{10}C(O)NR^7R^9$, —$NR^{10}C(NCN)NR^7R^9$, —$OR^9$, —$S(O)R^{13}$, —$S_2R^{13}$, aryl, arylalkyl, heteroaryl, heteroarylalkyl, heterocyclyl and heterocyclylalkyl; where $R^7$, $R^8$, $R^9$, $R^{10}$ and $R^{13}$ are the same as $R^7$, $R^8$, $R^9$, $R^{10}$ and $R^{13}$ defined above, provided that (i) when Q is $CR^3R^{11}R^{12}$ not more than one group among $R^3$, $R^{11}$ or $R^{12}$ may be simultaneously connected to C through a heteroatom, (ii) when Q is $CR^3R^{11}R^{12}$, $R^3$ may not be cyano or halogen, (iii) when Q is $NR^{11}R^{12}$, not more than one group between $R^{11}$ and $R^{12}$ may be connected to N through a heteroatom, and (iv) when L is $NR^{11}R^{12}$; and D represents hydrogen, trifluoromethyl, difluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, —$SO_2NR^9R^7$, —$C(O)R^9$, $C(O)OR^9$, —$OC(O)R^9$, or —$C(O)NR^7R^9$, where each alkyl, alkenyl, alkynyl, cycloalkyl, aryl, heteroaryl and heterocyclyl portion is optionally substituted with up to five groups independently selected from oxo, halogen, cyano, nitro, trifluoromethyl, difluoromethoxy, trifluoromethoxy, azido, —$NR^7SO_2R^8$, —$SO_2NR^9R^7$, —$C(O)R^9$, —$C(O)OR^9$, —$OC(O)R^9$, —$NR^7C(O)OR^9$, —$NR^7C(O)R^9$, —$C(O)NR^7R^9$, —$NR^7R^9$, —$NR^{10}C(O)NR^7R^9$, —$NR^{10}C(NCN)NR^7R^9$, —$OR^9$, —$S(O)R^{13}$, —$SO_2R^{13}$, aryl, arylalkyl, heteroaryl, heteroarylalkyl, heterocyclyl and heterocyclylalkyl, and where $R^7$, $R^8$, $R^9$, $R^{10}$ and $R^{13}$ are the same as $R^7$, $R^8$, $R^9$, $R^{10}$ and $R^{13}$ defined above, provided that when L is N, (i) D is hydrogen or is selected so that L binds to a carbon atom, and (ii) if m=1, T is selected so that L binds to a carbon atom.

2. The compound of claim 1, wherein m is 1, T is attached to the quinazoline ring at position 6, and T represents $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl; where each alkyl, alkenyl, alkynyl, cycloalkyl, aryl, heteroaryl and heterocyclyl portion is optionally substituted with one to five groups independently selected from oxo, halogen, cyano, nitro, trifluoromethyl, difluoromethoxy, trifluoromethoxy, azido, —$NR SO_2R^8$, —$SO_2NR^9R^7$, —$C(O)R^9$, —$C(O)OR^9$, —$OC(O)R^9$, —$NR^7C(O)OR^8$, —$NR^7C(O)R^9$, —$C(O)NR^7R^9$, —$NR^7R^9$, —$NR^{10}C(O)NR^7R^9$, —$NR^{10}C(NCN)NR^7R^9$, —$OR^9$, aryl, arylalkyl, heteroaryl, heteroarylalkyl, heterocyclyl, and heterocyclylalkyl.

3. The compound of claim 2, wherein L is N and D represents hydrogen.

4. The compound of claim 2, wherein $R^2$ is attached to the quinazoline ring at position 7.

5. The compound of claim 4, wherein $R^2$ represents —OMe.

6. A compound comprising

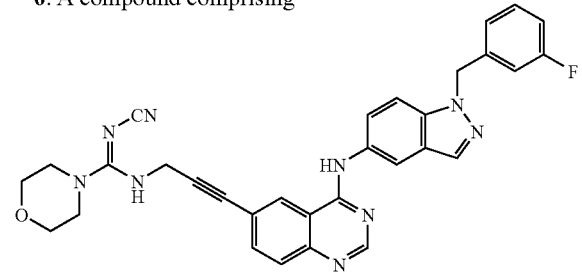

or a pharmaceutically acceptable salt thereof.

7. A compound comprising

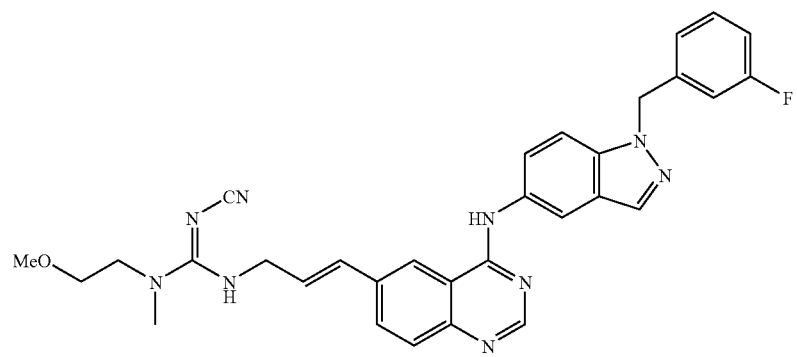

or a pharmaceutically acceptable salt thereof.

8. The compound of claim 2, wherein T is an optionally substituted $C_2$-$C_{10}$ alkenyl or $C_2$-$C_1$ alkynyl.

9. The compound of claim 8, wherein T is

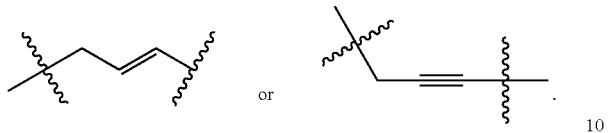

10. The compound of claim 2, wherein T is an optionally substituted heteroarylalkyl.

11. The compound of claim 10, wherein T is

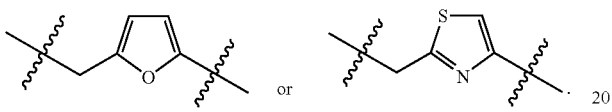

12. The compound of claim 2, wherein Q is $NR^{11}R^{12}$.

13. The compound of claim 12, wherein Q is —$NH_2$, —NHMe, —$NMe_2$, —$NH(CH_2CH_2OH)$, —$N(Me)(CH_2CH_2NMe_2)$, or —$N(Me)(CH_2CH_2OMe)$.

14. The compound of claim 1, wherein A is selected from:

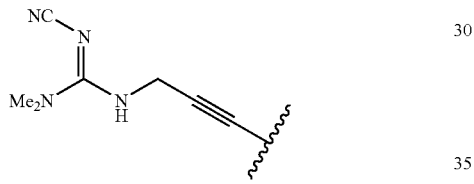

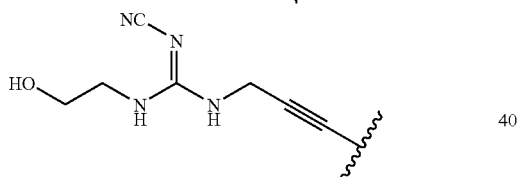

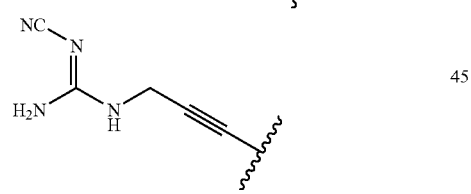

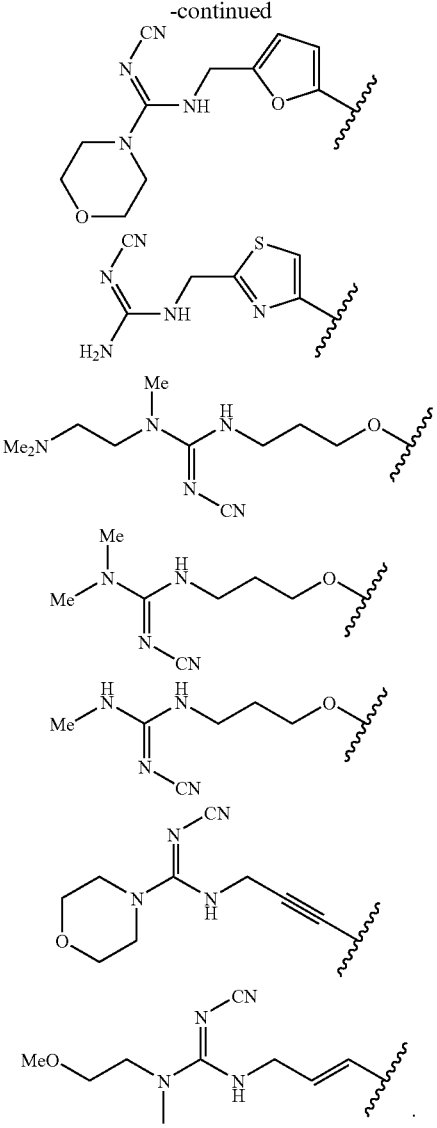

* * * * *